United States Patent
Boudreaux

(10) Patent No.: US 11,998,204 B2
(45) Date of Patent: Jun. 4, 2024

(54) COMPRESSIBLE ADJUNCT FOR SURGICAL STAPLER

(71) Applicant: Cilag GmbH International, Zug (CH)

(72) Inventor: Chad P. Boudreaux, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 17/514,126

(22) Filed: Oct. 29, 2021

(65) Prior Publication Data

US 2023/0140285 A1      May 4, 2023

(51) Int. Cl.
*A61B 17/072* (2006.01)
*A61B 17/00* (2006.01)

(52) U.S. Cl.
CPC ........ *A61B 17/07292* (2013.01); *A61B 2017/00473* (2013.01); *A61B 2017/07257* (2013.01); *A61B 2017/07271* (2013.01); *A61B 2017/07285* (2013.01)

(58) Field of Classification Search
CPC  A61B 2017/07257; A61B 2017/07271; A61B 2017/07285; A61B 17/07292; A61B 2017/0495
See application file for complete search history.

(56) References Cited

U.S. PATENT DOCUMENTS

| | | | |
|---|---|---|---|
| 5,711,960 A * | 1/1998 | Shikinami | A61L 27/00 428/36.1 |
| 7,147,138 B2 | 12/2006 | Shelton, IV | |
| 7,380,696 B2 | 6/2008 | Shelton, IV et al. | |
| 7,665,646 B2 | 2/2010 | Prommersberger | |
| 7,845,533 B2 | 12/2010 | Marczyk et al. | |
| 8,028,883 B2 | 10/2011 | Stopek | |
| 8,210,411 B2 | 7/2012 | Yates et al. | |
| 8,348,130 B2 | 1/2013 | Shah et al. | |
| 8,408,439 B2 | 4/2013 | Huang et al. | |

(Continued)

FOREIGN PATENT DOCUMENTS

| | | |
|---|---|---|
| EP | 3150143 A1 | 4/2017 |
| EP | 3791806 A1 | 3/2021 |

OTHER PUBLICATIONS

European Examination Report dated Sep. 14, 2023 for Application No. EP 22797890.5, 3 pgs.

(Continued)

*Primary Examiner* — Robert F Long
*Assistant Examiner* — Eduardo R Ferrero
(74) *Attorney, Agent, or Firm* — Frost Brown Todd LLP

(57) ABSTRACT

An adjunct configured for use with a surgical stapler end effector includes an adjunct body configured to overlie and directly contact a stapling surface of a surgical stapler end effector, and a plurality of resiliently compressible members coupled with the adjunct body. Each resiliently compressible member extends away from the adjunct body in a first plane that intersects the adjunct body and along which the resiliently compressible member is configured to receive a respective staple of the surgical stapler end effector. In response to closure of the surgical stapler end effector, each resiliently compressible member is configured to resiliently compress within the first plane without deforming in a second plane that perpendicularly intersects the first plane.

20 Claims, 19 Drawing Sheets

(56) References Cited

U.S. PATENT DOCUMENTS

| | | |
|---|---|---|
| 8,453,652 B2 | 6/2013 | Stopek |
| 8,453,914 B2 | 6/2013 | Laurent et al. |
| 8,479,968 B2 | 7/2013 | Hodgkinson et al. |
| 8,899,464 B2 | 12/2014 | Hueil et al. |
| 8,967,448 B2 | 3/2015 | Carter et al. |
| 9,055,941 B2 | 6/2015 | Schmid et al. |
| 9,186,142 B2 | 11/2015 | Fanelli et al. |
| 9,386,984 B2 | 7/2016 | Aronhalt et al. |
| 9,517,065 B2 | 12/2016 | Simms et al. |
| 9,585,657 B2 | 3/2017 | Shelton, IV et al. |
| 9,615,826 B2 | 4/2017 | Shelton, IV et al. |
| 9,622,746 B2 | 4/2017 | Simms et al. |
| 9,717,497 B2 | 8/2017 | Zerkle et al. |
| 9,795,379 B2 | 10/2017 | Leimbach et al. |
| 9,808,248 B2 | 11/2017 | Hoffman |
| 9,839,421 B2 | 12/2017 | Zerkle et al. |
| 10,092,292 B2 | 10/2018 | Boudreaux et al. |
| 10,172,620 B2 | 1/2019 | Harris et al. |
| 10,293,553 B2 | 5/2019 | Racenet et al. |
| 10,342,542 B2 | 7/2019 | Barton et al. |
| 10,349,939 B2 | 7/2019 | Shelton, IV et al. |
| 10,441,285 B2 | 10/2019 | Shelton, IV et al. |
| 10,485,544 B2 | 11/2019 | Shelton, IV et al. |
| 10,524,788 B2 | 1/2020 | Vendely et al. |
| 10,548,597 B2 | 2/2020 | Dunki-Jacobs et al. |
| 10,568,621 B2 | 2/2020 | Shelton, IV et al. |
| 10,588,623 B2 | 3/2020 | Schmid et al. |
| 10,624,861 B2 | 4/2020 | Widenhouse et al. |
| 10,667,808 B2 | 6/2020 | Baxter, III et al. |
| 10,709,452 B2 | 7/2020 | DiNardo et al. |
| 10,856,866 B2 | 12/2020 | Shelton, IV et al. |
| 10,869,663 B2 | 12/2020 | Shelton, IV et al. |
| 10,966,722 B2 | 4/2021 | Shelton, IV et al. |
| 11,006,954 B2 | 5/2021 | Landgrebe et al. |
| 11,033,266 B2 | 6/2021 | Jones et al. |
| 11,058,425 B2 | 7/2021 | Widenhouse et al. |
| 11,219,451 B2 | 1/2022 | Shelton, IV et al. |
| 11,272,927 B2 | 3/2022 | Swayze et al. |
| 11,432,815 B2 | 9/2022 | Courtwright et al. |
| 11,504,115 B2 | 11/2022 | Shelton, IV et al. |
| 11,660,093 B2 | 5/2023 | Bakos et al. |
| 11,672,538 B2 | 6/2023 | Baril |
| 2006/0173470 A1* | 8/2006 | Oray ............... A61B 17/07207 606/151 |
| 2009/0206143 A1* | 8/2009 | Huitema .......... A61B 17/07292 227/176.1 |
| 2012/0080336 A1 | 4/2012 | Shelton, IV et al. |
| 2012/0080493 A1* | 4/2012 | Shelton, IV ........... A61B 90/92 227/176.1 |
| 2012/0080503 A1* | 4/2012 | Woodard, Jr. ..... A61B 17/0643 227/181.1 |
| 2012/0083836 A1* | 4/2012 | Shelton, IV ......... A61B 17/072 206/339 |
| 2012/0241491 A1* | 9/2012 | Aldridge ............ A61B 17/1155 227/175.1 |
| 2012/0241496 A1* | 9/2012 | Mandakolathur Vasudevan ........ A61B 17/0684 227/176.1 |
| 2012/0241497 A1* | 9/2012 | Mandakolathur Vasudevan ........ A61B 17/07292 227/176.1 |
| 2012/0241502 A1* | 9/2012 | Aldridge ............... A61B 17/064 227/176.1 |
| 2012/0241505 A1* | 9/2012 | Alexander, III ... A61B 17/1155 227/179.1 |
| 2012/0253298 A1* | 10/2012 | Henderson ....... A61B 17/07292 604/93.01 |
| 2012/0318844 A1* | 12/2012 | Shelton, IV ..... A61B 17/00234 227/176.1 |
| 2013/0256373 A1 | 10/2013 | Schmid et al. |
| 2013/0256375 A1* | 10/2013 | Shelton, IV ........ A61B 17/0643 227/176.1 |
| 2014/0144968 A1* | 5/2014 | Shelton, IV ..... A61B 17/07292 227/175.1 |
| 2014/0224857 A1* | 8/2014 | Schmid .............. A61B 17/0686 227/176.1 |
| 2015/0133995 A1* | 5/2015 | Shelton, IV ..... A61B 17/07292 227/176.1 |
| 2015/0136832 A1* | 5/2015 | Baxter, III ......... A61B 17/0644 227/176.1 |
| 2015/0282810 A1* | 10/2015 | Shelton, IV ..... A61B 17/07207 227/180.1 |
| 2015/0297236 A1* | 10/2015 | Harris .............. A61B 17/07292 227/176.1 |
| 2016/0345976 A1* | 12/2016 | González ......... A61B 17/07207 |
| 2017/0055981 A1* | 3/2017 | Vendely ........... A61B 17/07292 |
| 2017/0055986 A1* | 3/2017 | Harris ................ A61B 17/1155 |
| 2017/0056008 A1* | 3/2017 | Shelton, IV ......... A61B 17/068 |
| 2017/0086835 A1* | 3/2017 | Harris ...................... B32B 3/20 |
| 2017/0086837 A1* | 3/2017 | Vendely ................ B32B 5/024 |
| 2017/0086838 A1* | 3/2017 | Harris .................. A61B 17/105 |
| 2017/0086841 A1* | 3/2017 | Vendely .................. B05D 1/007 |
| 2017/0086845 A1* | 3/2017 | Vendely ............... D01D 5/0023 |
| 2017/0367694 A1* | 12/2017 | Shelton, IV ..... A61B 17/07292 |
| 2018/0206844 A1* | 7/2018 | Harris ............. A61B 17/07292 |
| 2018/0235624 A1* | 8/2018 | Shelton, IV ..... A61B 17/07292 |
| 2019/0269403 A1* | 9/2019 | Baxter, III ....... A61B 17/00491 |
| 2020/0214706 A1 | 7/2020 | Vendely et al. |
| 2021/0077094 A1* | 3/2021 | Harris ................ A61B 17/0686 |
| 2022/0079579 A1* | 3/2022 | Shelton, IV .......... A61L 31/146 |
| 2023/0139479 A1 | 5/2023 | Seow et al. |
| 2023/0139613 A1 | 5/2023 | Seow et al. |

OTHER PUBLICATIONS

International Search Report and Written Opinion dated Jan. 5, 2023 for Application No. PCT/IB2022/060268, 13 pgs.
International Search Report and Written Opinion dated Jan. 5, 2023 for Application No. PCT/IB2022/060272, 15 pgs.
International Search Report and Written Opinion dated Jan. 5, 2023 for Application No. PCT/IB2022/060274, 16 pgs.

\* cited by examiner

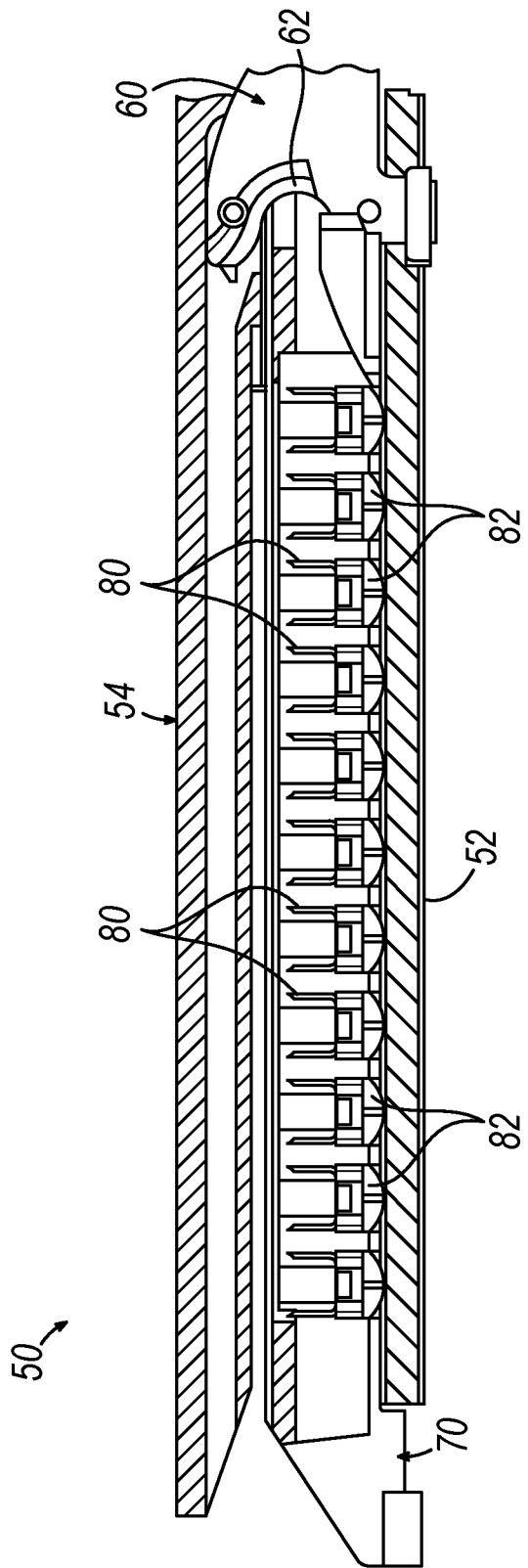

COMPRESSIBLE ADJUNCT FOR SURGICAL STAPLER

BACKGROUND

In some surgical settings, endoscopic surgical instruments may be preferred over traditional open surgical devices in order to make use of a smaller incision in the patient, which may reduce post-operative recovery time and complications. Some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 7,380,696, entitled "Articulating Surgical Stapling Instrument Incorporating a Two-Piece E-Beam Firing Mechanism," issued Jun. 3, 2008; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. Patents and U.S. Patent Publications is incorporated by reference herein.

Surgical staplers may also be used in open procedures and/or other non-endoscopic procedures. By way of example only, a surgical stapler may be inserted through a thoracotomy and thereby between a patient's ribs to reach one or more organs in a thoracic surgical procedure that does not use a trocar as a conduit for the stapler. For instance, the vessels leading to an organ may be severed and closed by a stapler before removal of the organ from the thoracic cavity. Of course, surgical staplers may be used in various other settings and procedures.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 5A depicts a side cross-sectional view of the end effector of FIG. 3, taken along line 5-5 of FIG. 3, with a firing member in a proximal position;

Figure 1:
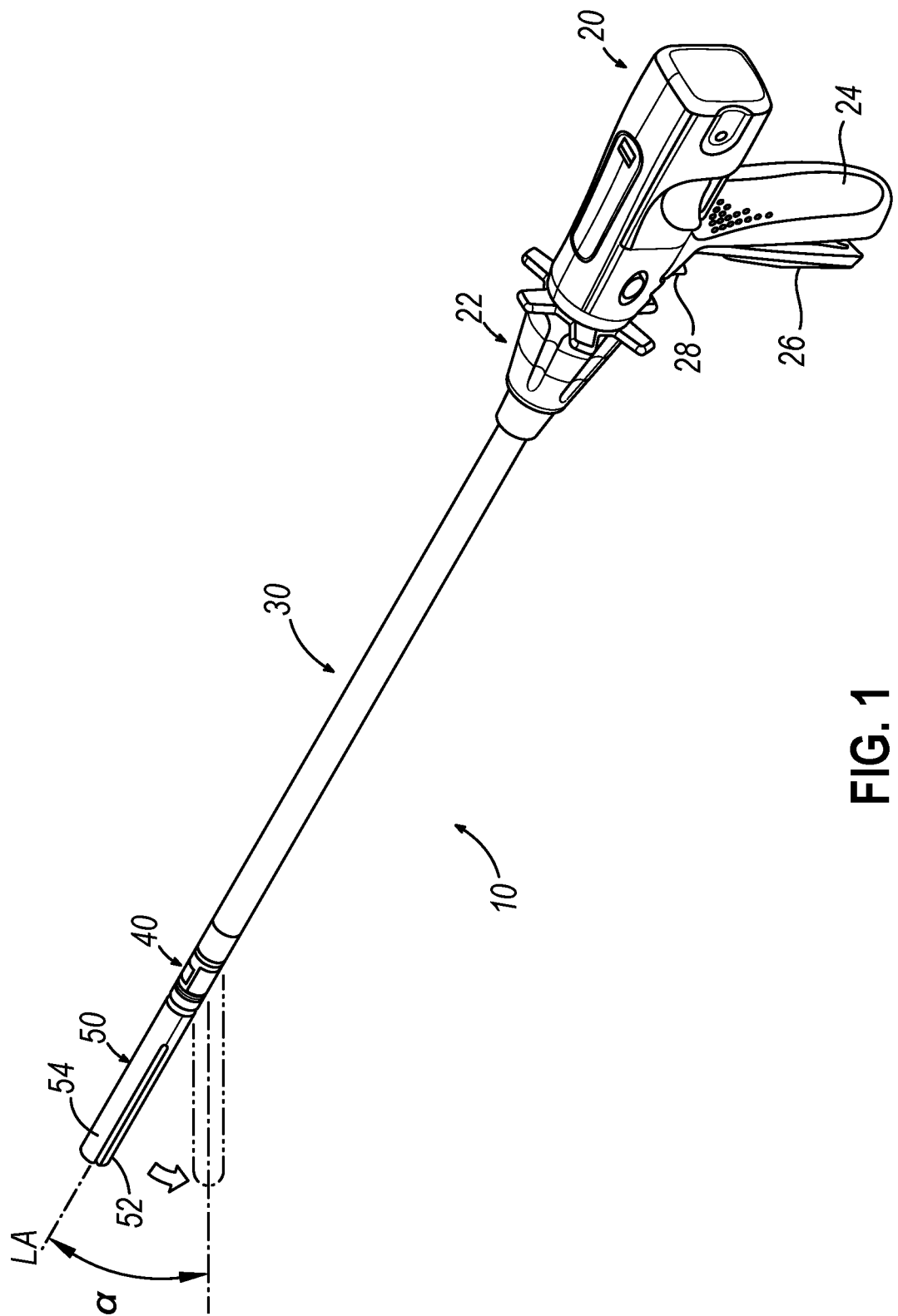
FIG. 1 depicts a perspective view of an exemplary surgical stapler.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. In addition, the terms "upper," "lower," "lateral," "transverse," "bottom," "top," are relative terms to provide additional clarity to the figure descriptions provided below. The terms "upper," "lower," "lateral," "transverse," "bottom," "top," are thus not intended to unnecessarily limit the invention described herein.

I. Examplary Surgical Stapler

Figure 2:
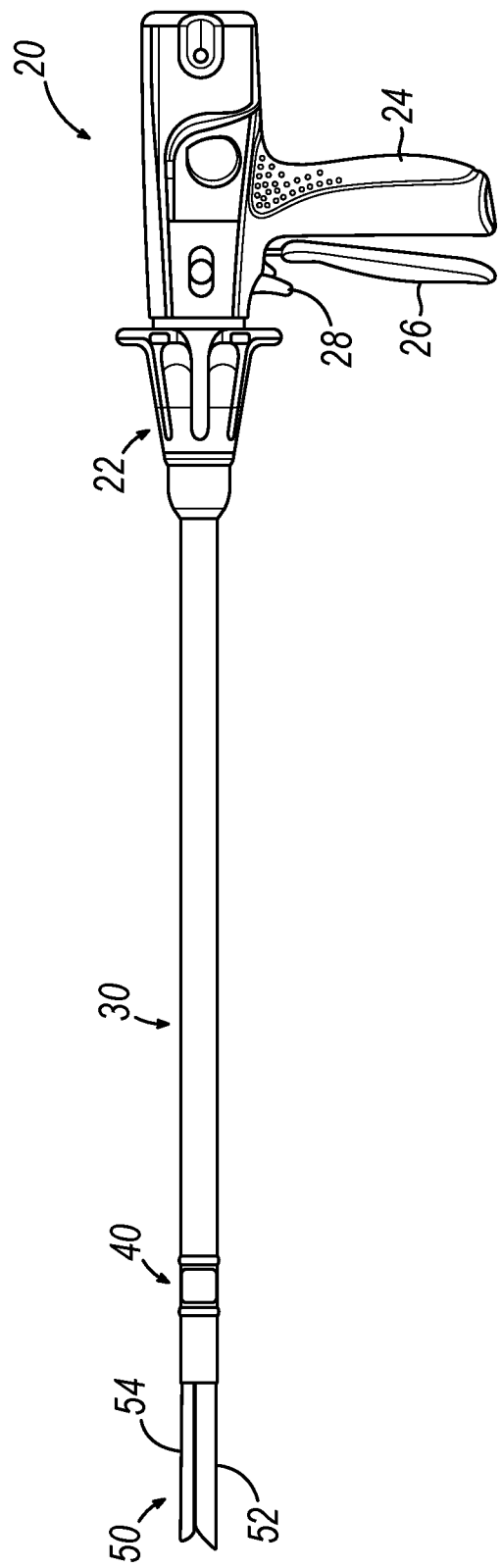
FIG. 2 depicts a side elevational view of the surgical stapler of FIG. 1.

FIGS. 1-6 show an exemplary surgical stapler (10) that is sized for insertion through a trocar cannula or an incision (e.g., thoracotomy, etc.) to a surgical site in a patient for performing a surgical procedure. As shown in FIGS. 1 and 2, surgical stapler (10) of the present example includes a proximal body in the form of a handle assembly (20), a shaft assembly (30) extending distally from handle assembly (20) and terminating at an articulation joint (40), and an end effector (50) coupled with the distal end of shaft assembly (30) via articulation joint (40). Articulation joint (40) is configured to enable lateral deflection, either actively or passively, of end effector (50) relative to a longitudinal axis (LA) of shaft assembly (30) to a desired angle (α) via actuation of an articulation control feature (22) of handle assembly (20).

Figure 3:
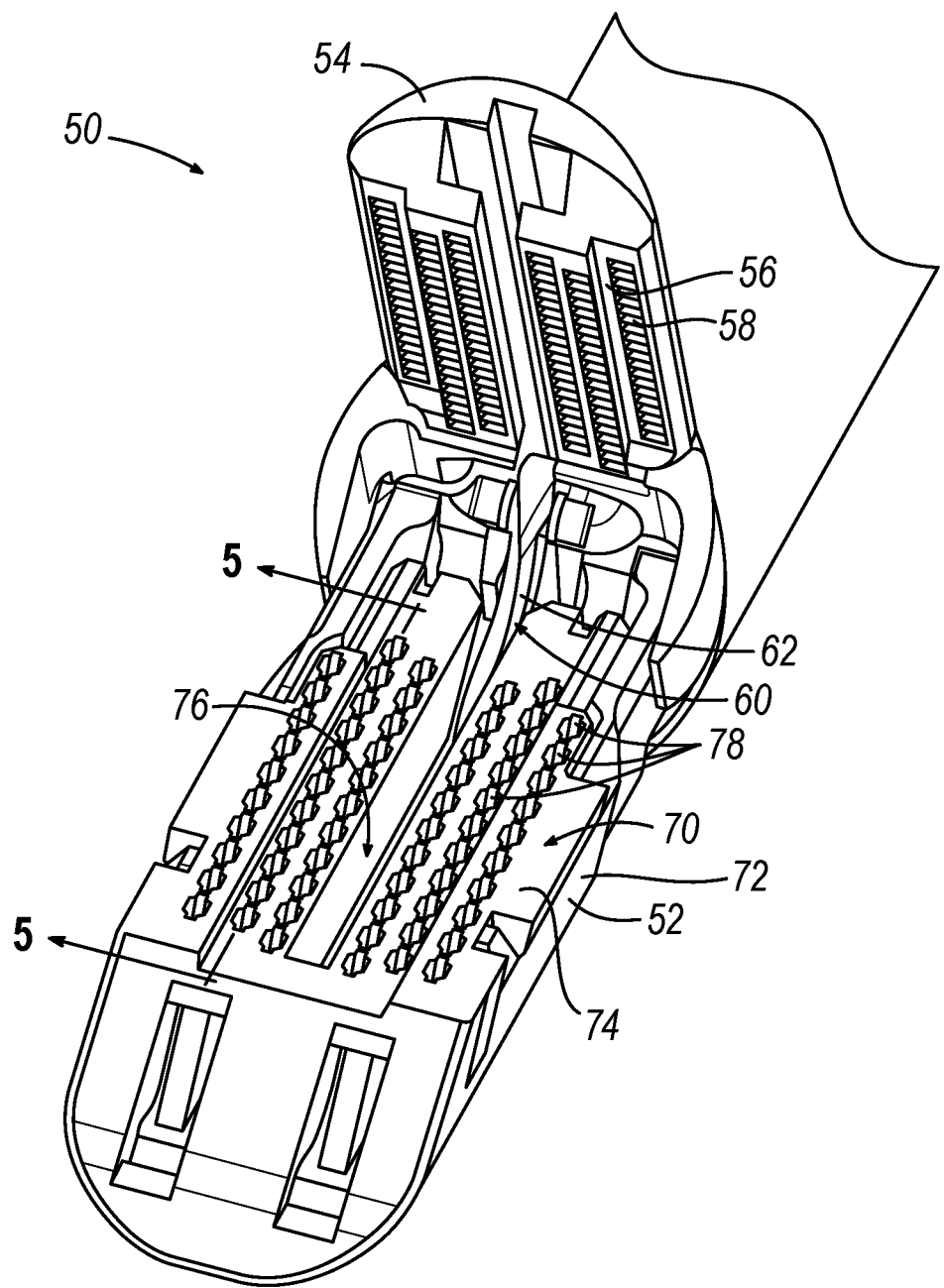
FIG. 3 depicts a perspective view of an end effector of the surgical stapler of FIG. 1 in an open state.
Figure 4:
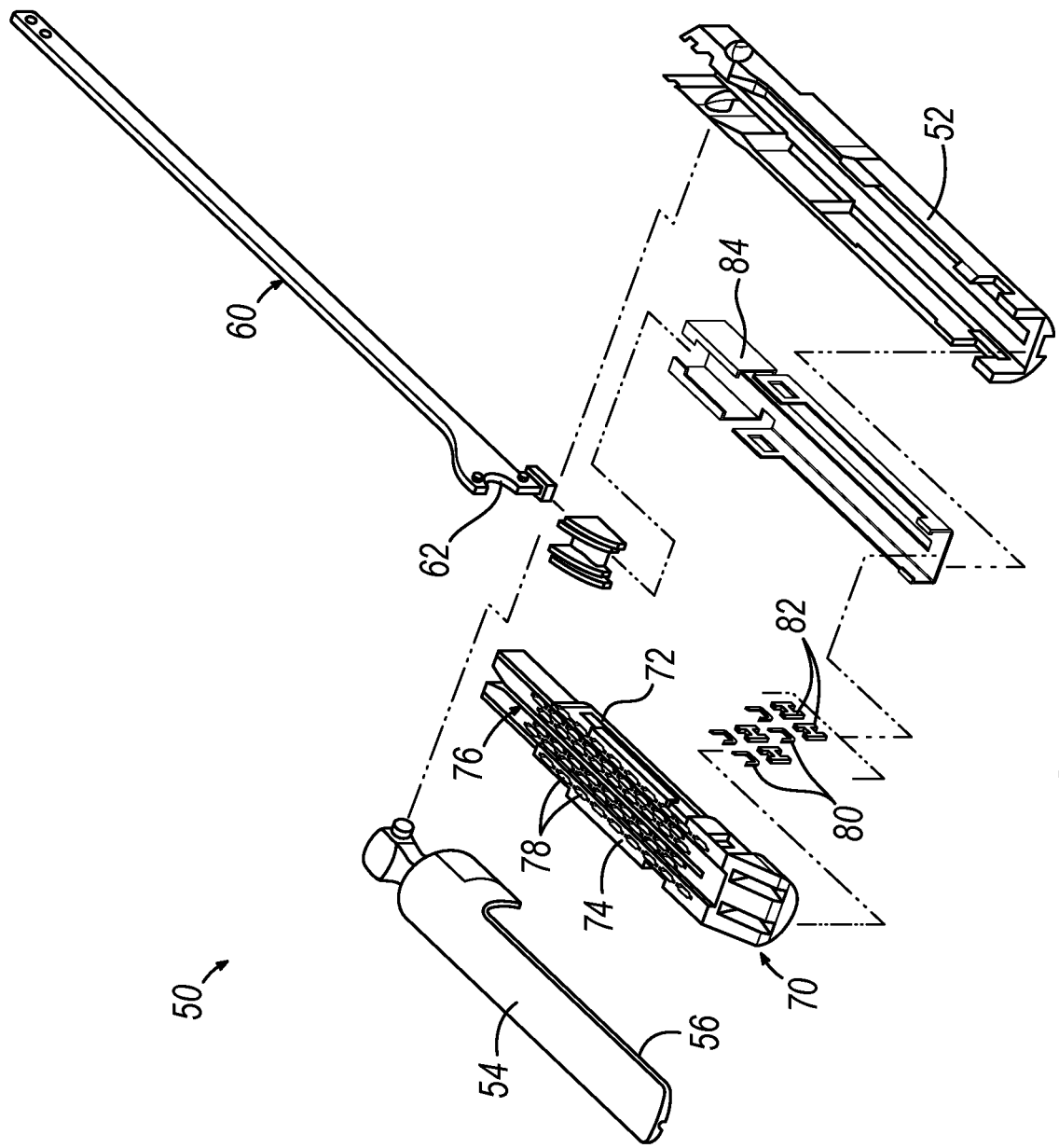
FIG. 4 depicts an exploded perspective view of the end effector of FIG. 3.

As shown best in FIGS. 3 and 4, end effector (50) includes a lower jaw (52) that supports a stapling assembly in the form of a replaceable staple cartridge (70), and an upper jaw (54) that presents an anvil (56) having a plurality of staple forming pockets (58). Upper jaw (54) is configured to pivot relative to lower jaw (52) to clamp tissue between staple cartridge (70) and anvil (56) and subsequently form staples deployed by staple cartridge (70). End effector (50) further includes an elongate firing member (60) configured to translate distally through end effector (50) to drive staples from staple cartridge (70) toward anvil (56) and simultaneously cut tissue with a distally presented cutting edge (62). Accordingly, end effector (50) is operable to clamp, staple, and cut tissue.

As shown best in FIGS. 1 and 2, handle assembly (20) further includes a pistol grip (24), a closure trigger (26), and a firing trigger (28). Closure trigger (26) is pivotable toward pistol grip (24) to pivotably actuate jaw (54) toward lower jaw (16) and thereby close end effector (50) on tissue. Firing trigger (28) is then pivotable toward pistol grip (24) to fire end effector (50) on the clamped tissue. More specifically, actuation of firing trigger (28) causes firing member (60) to translate distally through end effector (50), including staple cartridge (70), to thereby staple and simultaneously cut the clamped tissue.

As shown in FIGS. 3-5B, staple cartridge (70) includes a cartridge body (72) having an upwardly facing deck (74), an elongate slot (76) extending along a central axis of cartridge body (72) and opening upwardly through deck (74), and a plurality of staple openings (78) (also known as apertures) extending through deck (74) on each side of elongate slot (76). Each staple opening (78) slidably houses an unformed staple (80) and a respective staple driver (82) positioned beneath staple (80). A lower tray (84), also known as a pan, encloses an underside of cartridge body (72) and thereby retains staples (80) and staple drivers (82) within cartridge body (72). A wedge sled (86) is slidably disposed within cartridge body (72) and includes upwardly presented cam surfaces configured to engage the undersides of staple drivers (82).

Figure 5B:
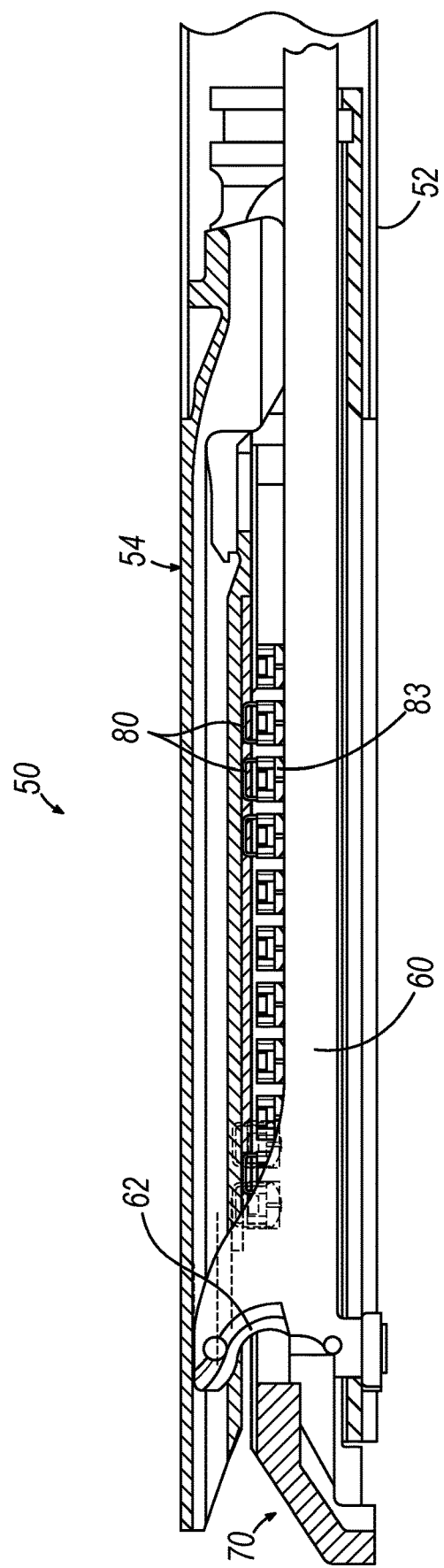
FIG. 5B depicts a side cross-sectional view of the end effector of FIG. 3, taken along line 5-5 of FIG. 3, with the firing member in a distal position.

FIGS. 5A-5B show a firing stroke of surgical stapler (10) during which firing member (60) is actuated distally through end effector (50), including elongate slot (76) of staple cartridge (70). A distal end of firing member (60) drives wedge sled (86) distally to cam staple drivers (82) upwardly and thereby drive the respective staples (80) outwardly from staple openings (78). The legs of staples (80) pass through clamped tissue (not shown) and are then formed by staple forming pockets (58) of anvil (56) (see FIG. 3). Simultaneously, the clamped tissue is severed by cutting edge (62) of firing member (60).

Figure 6:
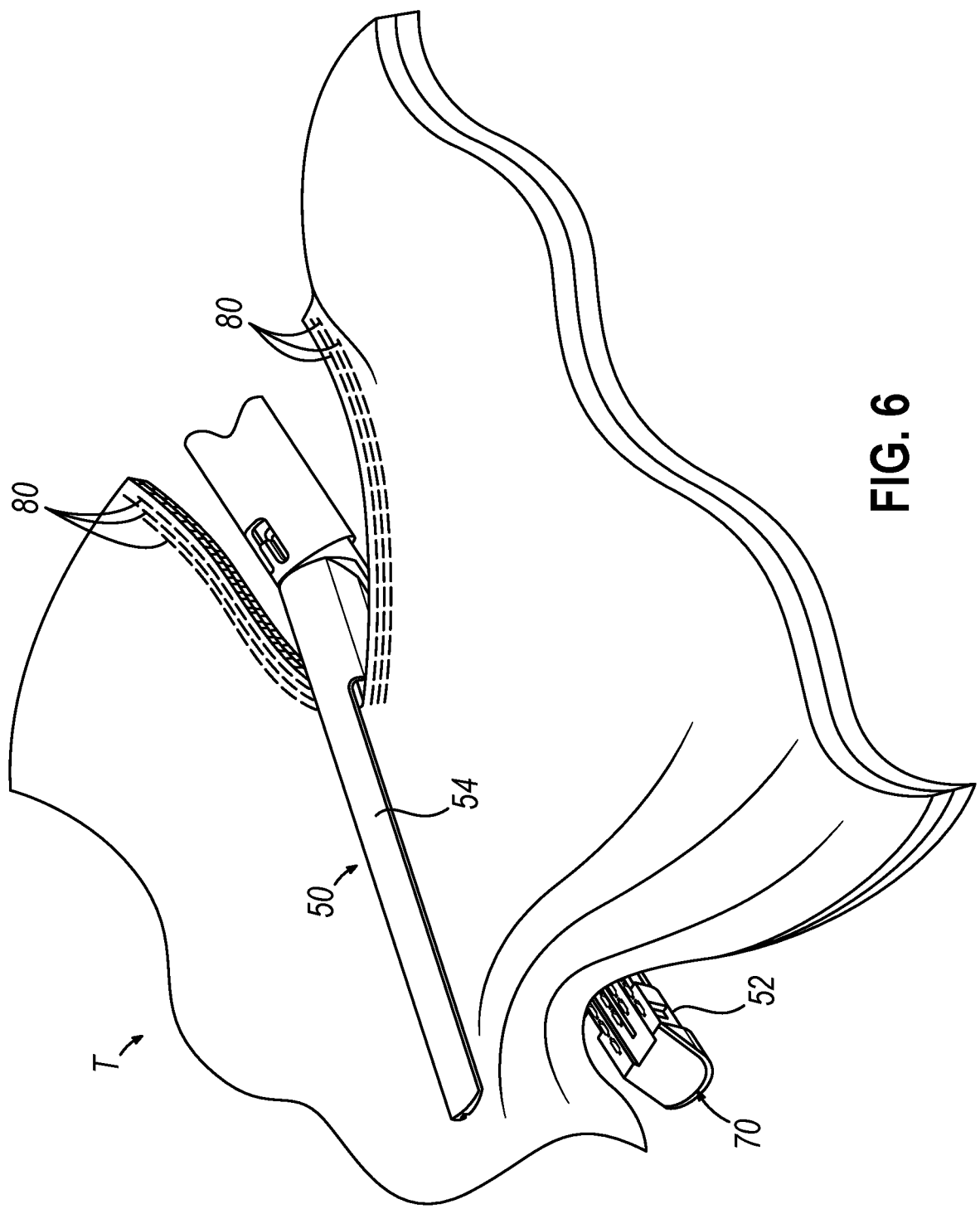
FIG. 6 depicts a perspective view of the end effector of FIG. 3, positioned at tissue and having been fired once in the tissue.

FIG. 6 shows end effector (50) after having been actuated through a single firing stroke through tissue (T). Cutting edge (62) of firing member (60) has cut through tissue (T), and staple drivers (82) have driven three alternating rows of staples (80) through tissue (T) on each side of the cut line produced by cutting edge (62). After the first firing stroke is completed, end effector (50) is withdrawn from the patient, spent staple cartridge (70) is replaced with a new staple cartridge (70), and end effector (50) is then again inserted into the patient to reach the stapling site for further cutting and stapling. This process may be repeated until the desired quantity and pattern of firing strokes across the tissue (T) has been completed.

Surgical stapler (10) may be further constructed and operable in accordance with any of the teachings of the following references, the disclosures of which are incorporated by reference herein: U.S. Pat. No. 8,210,411, entitled "Motor-Driven Surgical Instrument," issued Jul. 3, 2012; U.S. Pat. No. 9,186,142, entitled "Surgical Instrument End Effector Articulation Drive with Pinion and Opposing Racks," issued on Nov. 17, 2015; U.S. Pat. No. 9,517,065, entitled "Integrated Tissue Positioning and Jaw Alignment Features for Surgical Stapler," issued Dec. 13, 2016; U.S. Pat. No. 9,622,746, entitled "Distal Tip Features for End Effector of Surgical Instrument," issued Apr. 18, 2017; U.S. Pat. No. 9,717,497, entitled "Lockout Feature for Movable Cutting Member of Surgical Instrument," issued Aug. 1, 2017; U.S. Pat. No. 9,795,379, entitled "Surgical Instrument with Multi-Diameter Shaft," issued Oct. 24, 2017; U.S. Pat. No. 9,808,248, entitled "Installation Features for Surgical Instrument End Effector Cartridge," issued Nov. 7, 2017; U.S. Pat. No. 9,839,421, entitled "Jaw Closure Feature for End Effector of Surgical Instrument," issued Dec. 12, 2017; and/or U.S. Pat. No. 10,092,292, entitled "Staple Forming Features for Surgical Stapling Instrument," issued Oct. 9, 2018.

II. Exemplary Buttress Assembly

In some instances, it may be desirable to equip end effector (50) of surgical stapler (10) with an adjunct, also known as a buttress or a tissue thickness compensator, to reinforce the mechanical fastening of tissue provided by staples (80). Such a buttress may prevent the applied staples (80) from pulling through the tissue and may otherwise reduce a risk of tissue tearing at or near the site of applied staples (80). In addition to or as an alternative to providing structural support and integrity to a line of staples (80), a buttress may provide various other kinds of effects such as spacing or gap-filling, administration of therapeutic agents, and/or other effects. In some instances, a buttress may be provided on upper deck (74) of staple cartridge (70). In some other instances, a buttress may be provided on the surface of anvil (56) that faces staple cartridge (70). It should also be understood that a first buttress may be provided on upper deck (74) of staple cartridge (70) while a second buttress is provided on anvil (56) of the same end effector (50).

A. Exemplary Composition of Buttress Assembly

Figure 7:
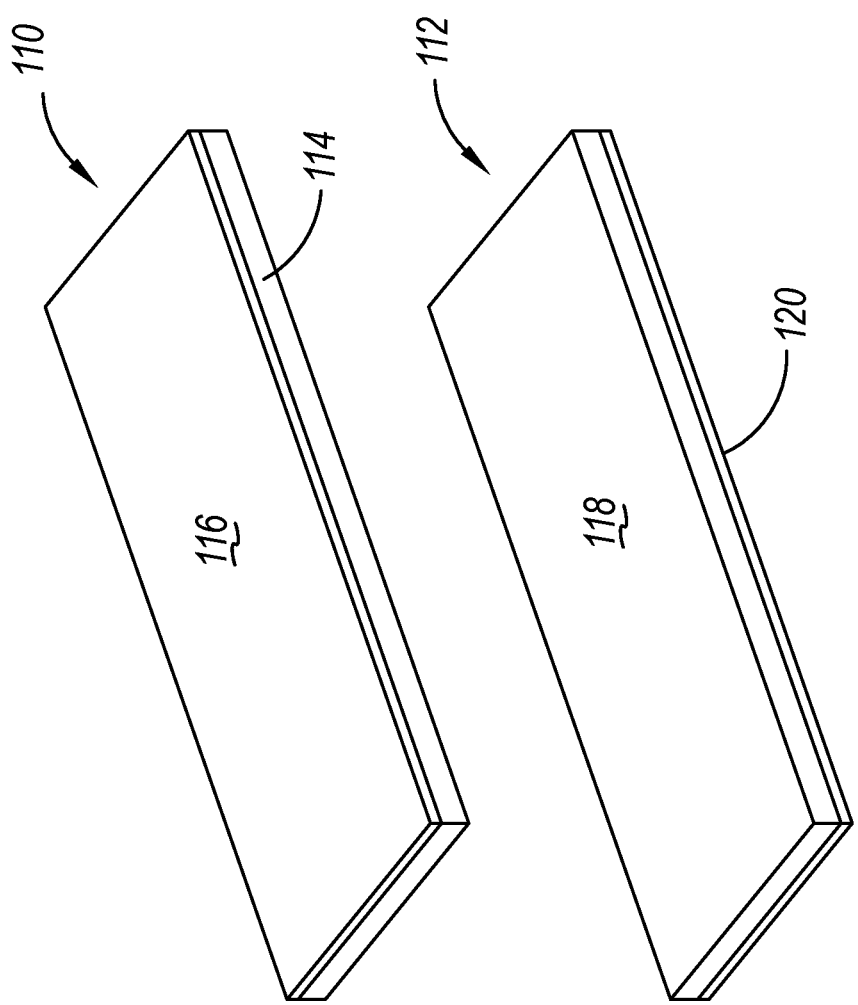
FIG. 7 depicts a perspective view of an exemplary pair of adjuncts in the form of buttress assemblies, each of which may be applied to a jaw of the end effector of FIG. 3.

FIG. 7 shows an exemplary pair of adjuncts in the form of buttress assemblies (110, 112) (each also referred to individually as a "buttress"). Buttress assembly (110) of this example comprises a buttress body (114) and an upper adhesive layer (116). Similarly, buttress assembly (112) comprises a buttress body (118) and a lower adhesive layer (120). In the present example, each buttress body (114, 118) comprises a strong yet flexible material configured to structurally support a line of staples (80). By way of example only, each buttress body (114, 118) may comprise a mesh of polyglactin 910 material by Ethicon, Inc. of Somerville, New Jersey. Alternatively, any other suitable materials or combinations of materials may be used in addition to or as an alternative to polyglactin 910 material to form each buttress body (114, 118).

Each buttress body (114, 118) may comprise a material including, for example, a hemostatic agent such as fibrin to assist in coagulating blood and reduce bleeding at the severed and/or stapled surgical site along tissue ($T_1$, $T_2$). As another merely illustrative example, each buttress body (114, 118) may comprise other adjuncts or hemostatic agents such as thrombin may be used such that each buttress body (114, 118) may assist to coagulate blood and reduce the amount of bleeding at the surgical site. Other adjuncts or reagents that may be incorporated into each buttress body (114, 118) may further include but are not limited to medical fluid or matrix components.

In the present example, adhesive layer (116) is provided on buttress body (114) to adhere buttress body (114) to an underside (124) of anvil (56). Similarly, adhesive layer (120) is provided on buttress body (118) to adhere buttress body (118) to upper deck (74) of staple cartridge (70). Such an adhesive material may provide proper positioning of buttress body (114, 118) before and during actuation of end effector (50); then allow buttress body (114, 118) to separate from end effector (50) after end effector (50) has been actuated, without causing damage to buttress body (114, 118) that is substantial enough to compromise the proper subsequent functioning of buttress body (114, 118).

B. Exemplary Stapling of Tissue with Buttress Assemblies

Figure 8C:
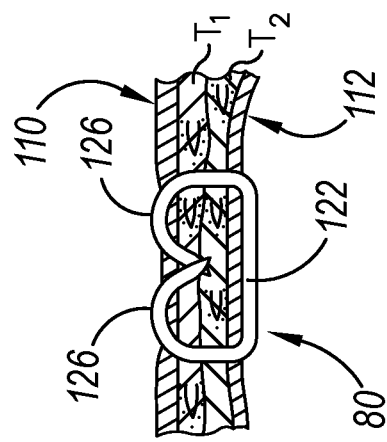
FIG. 8C depicts a cross-sectional view of a formed staple and the buttress assemblies of FIG. 8A after having been secured to the tissue by the end effector of FIG. 3.
Figure 8B:
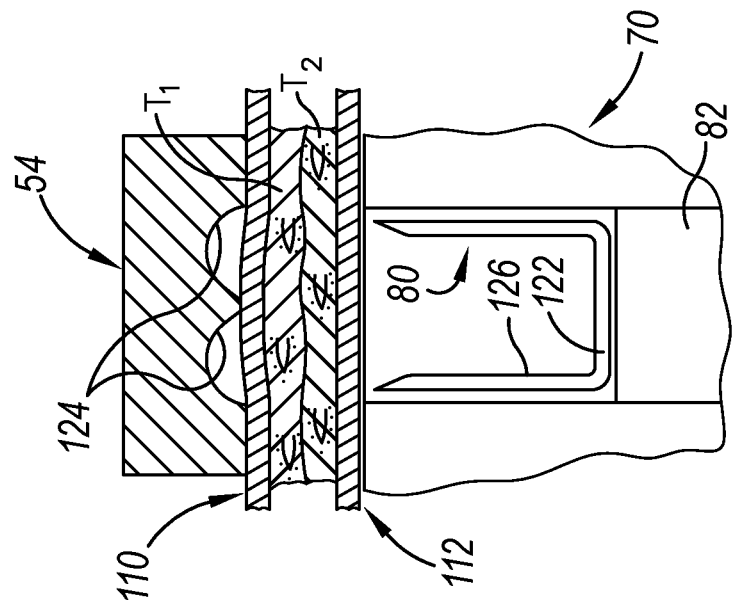
FIG. 8B depicts a cross-sectional end view of the end effector and buttress assemblies of FIG. 8A, showing the end effector jaws in a closed state on the tissue.
Figure 8A:
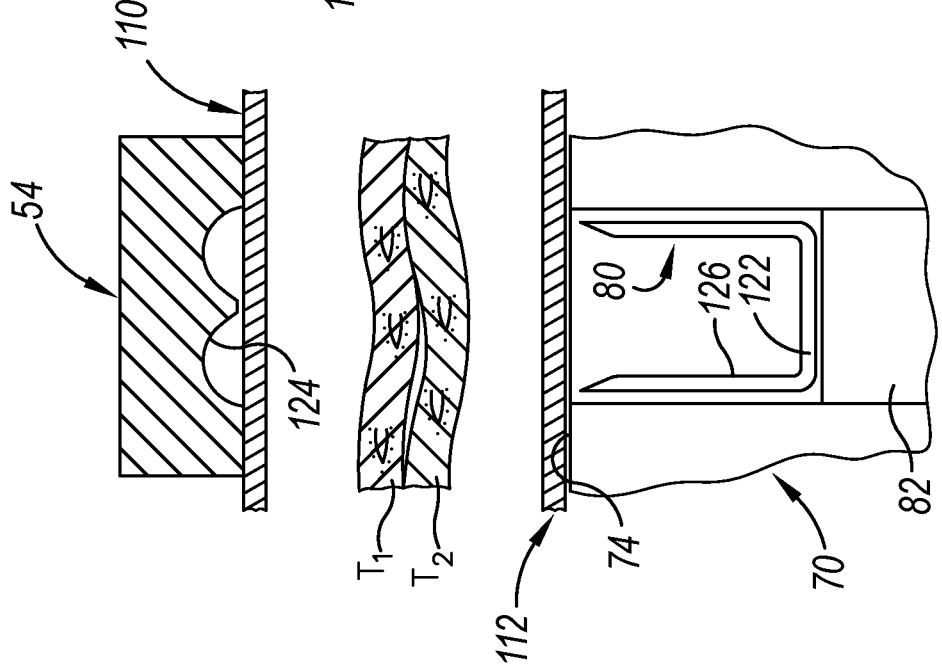
FIG. 8A depicts a cross-sectional end view of a portion of the end effector of FIG. 3 with the buttress assemblies of FIG. 7 applied to the upper and lower jaws of the end effector, showing the end effector jaws in an open state with tissue positioned between the upper and lower jaws.

FIGS. 8A-8C show an exemplary sequence in which surgical stapler end effector (50), which has been loaded with buttress assemblies (110, 112), is actuated to drive staples (80) through two opposed layers of tissue ($T_1$, $T_2$), with buttress assemblies (110, 112) being secured to the same layers of tissue ($T_1$, $T_2$) by staples (80). In particular, FIG. 8A shows layers of tissue ($T_1$, $T_2$) positioned between anvil (56) and staple cartridge (70), with anvil (56) in the open position. Buttress assembly (110) is adhered to underside (124) of anvil (56) via adhesive layer (116); while buttress assembly (112) is adhered to upper deck (74) of staple cartridge (70) via adhesive layer (120). Layers of tissue ($T_1$, $T_2$) are thus interposed between buttress assemblies (110, 112). Next, anvil (56) is closed against staple cartridge (70) such that layers of tissue ($T_1$, $T_2$) are compressed between anvil (56) and staple cartridge (70), with buttress assemblies (110, 112) engaging opposite surfaces of tissue layers ($T_1$, $T_2$). End effector (50) is then fired as described above, driving staple (80) through buttress assemblies (110, 112) and tissue ($T_1$, $T_2$). As shown in FIG. 8C, a crown (122) of driven staple (80) captures and retains buttress assembly (112) against layer of tissue ($T_2$). Deformed legs (126) of staple (80) capture and retain buttress assembly (110) against layer of tissue ($T_1$).

Figure 9:
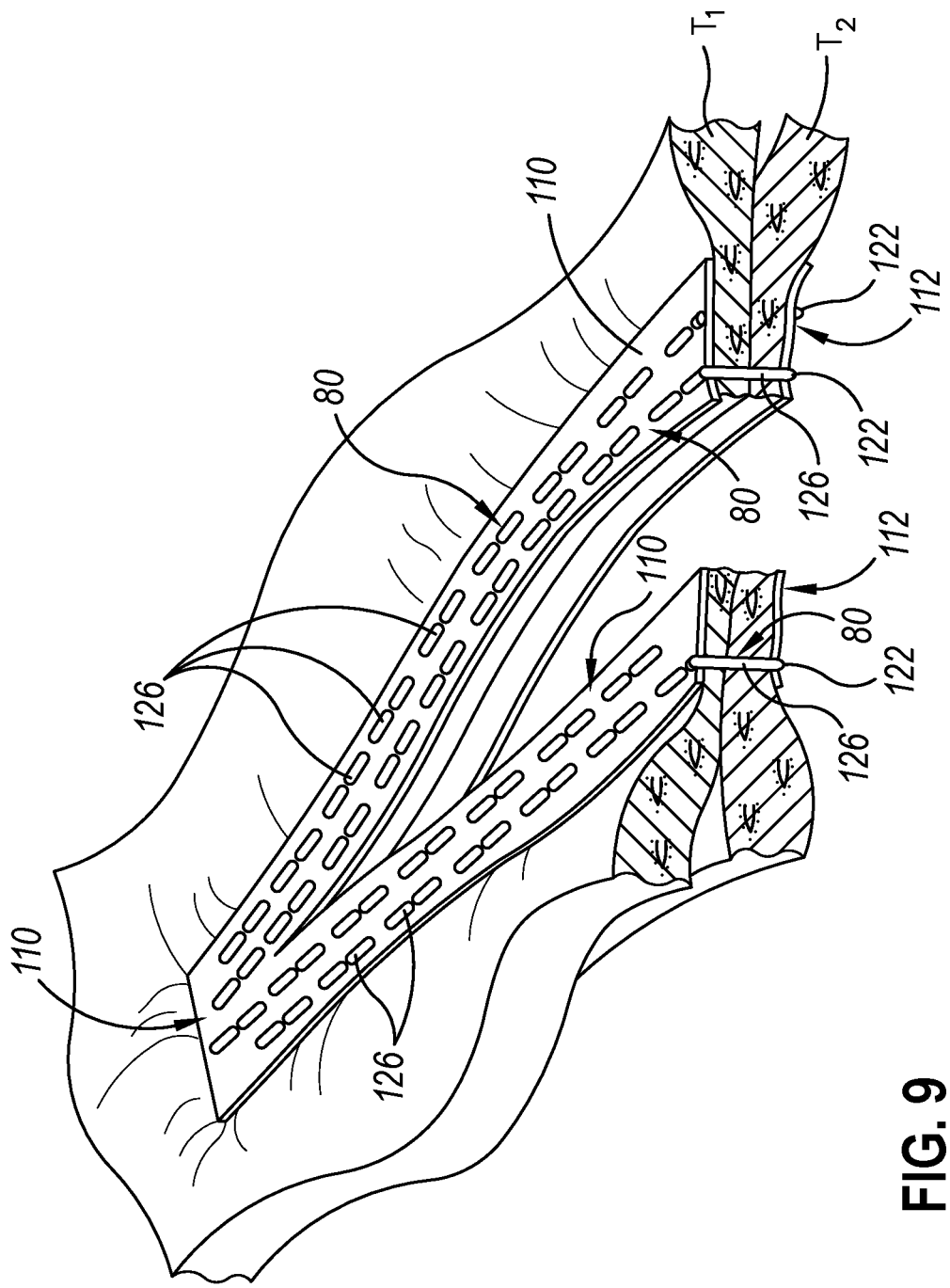
FIG. 9 depicts a perspective view of formed staples and the buttress assemblies of FIG. 8A after having been secured to the tissue by the end effector of FIG. 3.
Figure 10:
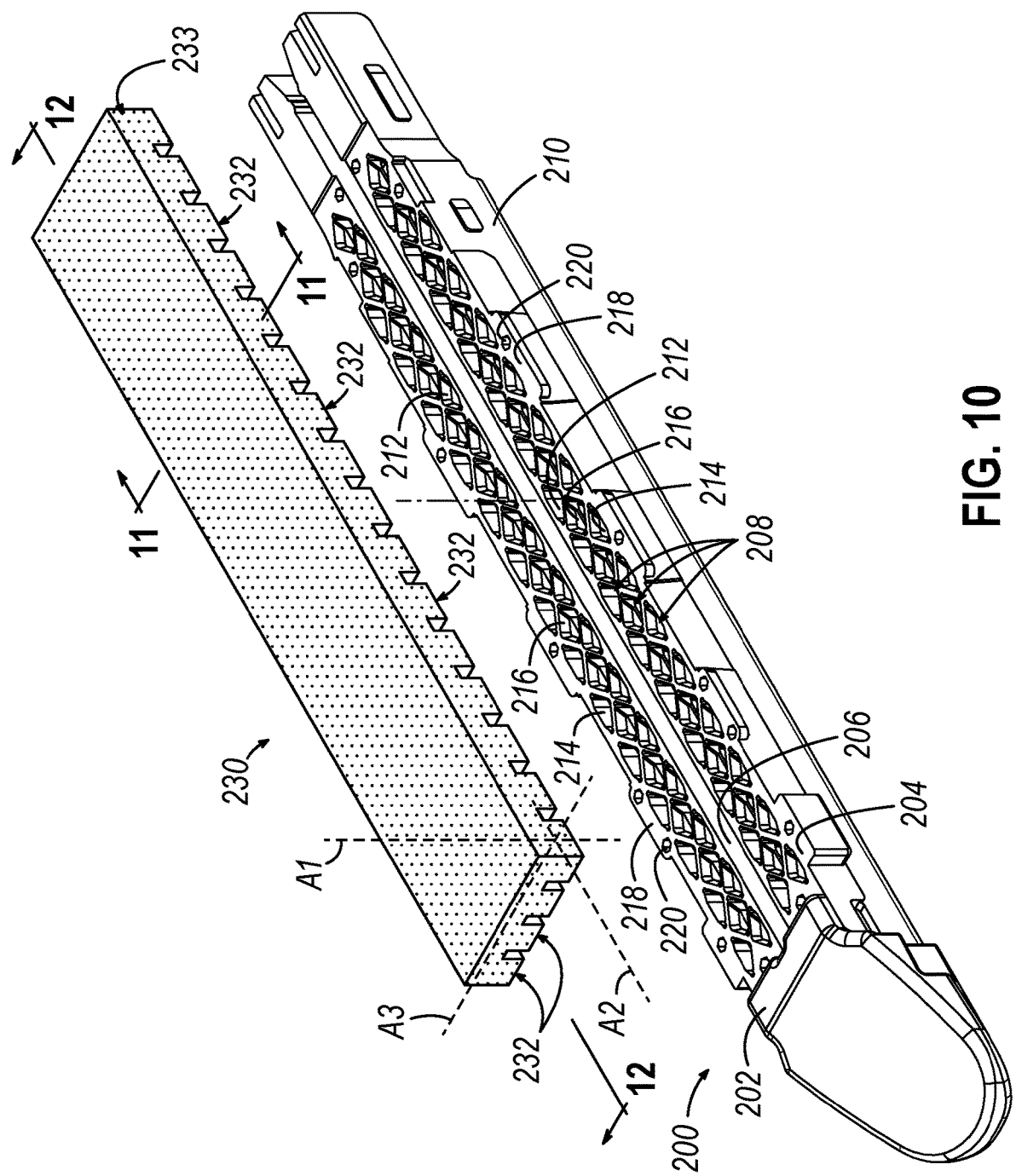
FIG. 10 depicts a disassembled perspective view of another exemplary staple cartridge in combination with another exemplary adjunct.

A series of staples (80) similarly capture and retain buttress assemblies (110, 112) against layers of tissue ($T_1$, $T_2$), thereby securing buttress assemblies (110, 112) to tissue ($T_1$, $T_2$) as shown in FIG. 10. As end effector (50) is pulled away from tissue ($T_1$, $T_2$) after deploying staples (80) and buttress assemblies (110, 112), buttress assemblies (110, 112) disengage end effector such that buttress assemblies (110, 112) remain secured to tissue ($T_1$, $T_2$) with staples (80). Buttress assemblies (110, 112) thus provide structural reinforcement to the lines of staples (80) formed in tissue ($T_1$, $T_2$). As can also be seen in FIG. 9, distally presented cutting edge (62) of firing member (60) also cuts through a centerline of buttress assemblies (110, 112), separating each buttress assembly (110, 112) into a corresponding pair of sections, such that each section remains secured to a respective severed region of tissue ($T_1$, $T_2$).

During use, surgical instrument (10) may be actuated multiple times during a single surgical procedure such that it may be desirable to enable an operator to repeatedly and easily load buttress assemblies (110, 112) onto lower jaw and anvil (16, 18) during that single surgical procedure. Accordingly, it may be desirable to use an adjunct applicator, also referred to as a buttress applier cartridge, to apply buttress assemblies (110, 112) to lower jaw and anvil (16, 18). Exemplary versions of such an applicator are disclosed in U.S. patent application Ser. No. 17/022,520, entitled "Method of Applying Buttress to End Effector of Surgical Stapler," filed Sep. 16, 2020, the disclosure of which is incorporated by reference herein.

It will be appreciated that exemplary adjuncts and adjunct applicators may be further configured in accordance with one or more teachings of U.S. Pat. No. 10,166,023, entitled "Method of Applying a Buttress to a Surgical Stapler End Effector," issued Jan. 1, 2019; U.S. Pat. No. 10,349,939, entitled "Method of Applying a Buttress to a Surgical Stapler," issued Jul. 16, 2019; and U.S. Pat. Pub. No. 2012/0080336, entitled "Staple Cartridge Comprising Staples Positioned Within a Compressible Portion Thereof," published Apr. 5, 2012, now abandoned, the disclosures of which are incorporated by reference herein.

III. Exemplary Comressible Adjunct

Figure 11:
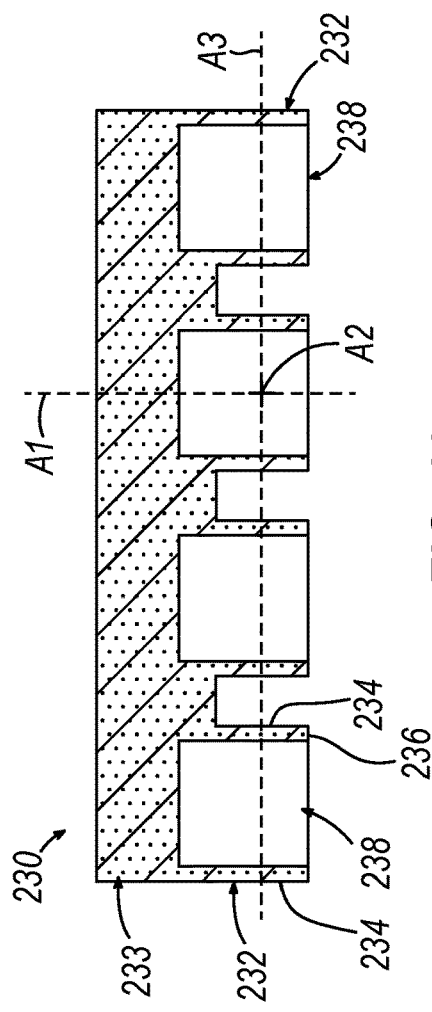
FIG. 11 depicts an end elevational view of the adjunct of FIG. 10.
Figure 12:
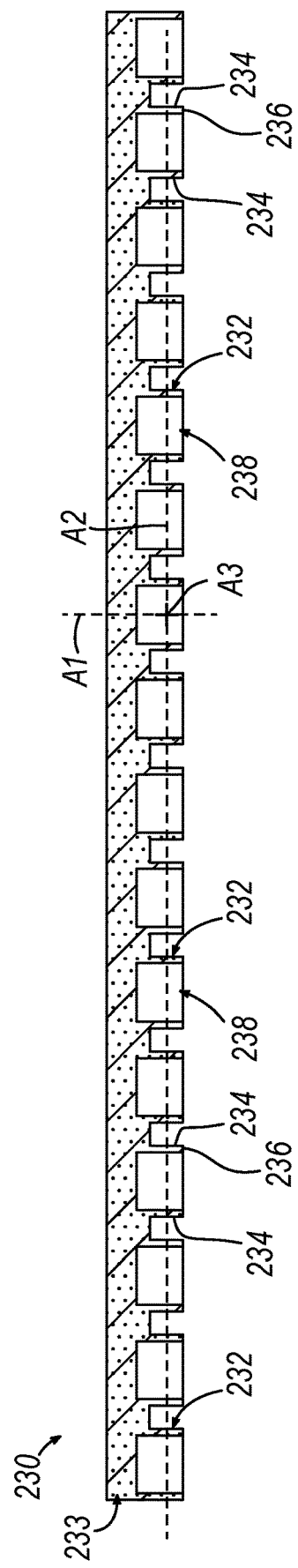
FIG. 12 depicts a side elevational view of the adjunct of FIG. 10.

In some instances, it may be desirable to employ an adjunct having an enhanced degree of compressibility in a direction orthogonal to the stapling surfaces of end effector (50). Such an adjunct may be configured to apply a compression spring force to stapled tissue consistently along the entire length of the formed staple pattern, thereby ensuring a secure seal of tissue having a thickness that varies along a length of the formed staple pattern and end effector (50). FIGS. 10-12 show an example of such an adjunct (230), also referred to herein as a buttress or cushion, in combination with a staple cartridge (200). Staple cartridge (200) and adjunct (230) are configured for use with end effector (50) and are similar to staple cartridge (70) and buttress assembly (110, 112) described above except as otherwise described below.

It will be appreciated that staple cartridge (200) and/or adjunct (230) may be further configured in accordance with teachings of any one of more the following references, the disclosures of which are incorporated by reference herein: U.S. Pat. No. 10,441,285, entitled "Tissue Thickness Compensator Comprising Tissue Ingrowth Features," issued Oct. 15, 2019; U.S. Pat. No. 10,524,788, entitled "Compressible Adjunct with Attachment Regions," issued Jan. 7, 2020; U.S. Pat. No. 10,568,621, entitled "Surgical Staple Buttress with Integral Adhesive for Releasably Attaching to a Surgical Stapler," issued Feb. 25, 2020; U.S. Pat. No. 10,588,623, entitled "Adhesive Film Laminate," issued Mar. 17, 2020; U.S. Pat. No. 10,624,861, entitled "Tissue Thickness Compensator Configured to Redistribute Compressive Forces," issued Apr. 21, 2020; U.S. Pat. No. 10,667,80, entitled "Staple Cartridge Comprising an Absorbable Adjunct," issued Jun. 2, 2020; U.S. Pat. No. 10,945,731, entitled "Tissue Thickness Compensator Comprising Controlled Release and Expansion," issued Mar. 16, 2021; U.S. Pat. No. 10,966,722, entitled "Adjunct Materials and Methods of Using Same in Surgical Methods for Tissue Sealing," issued Apr. 6, 2021; U.S. Pat. No. 11,058,425, entitled "Implantable Layers for a Surgical Instrument," issued Jul. 13, 2021; and U.S. Pat. Pub. No. 2019/0200978, entitled "Tissue Ingrowth Materials and Method of Using the Same," published Jul. 4, 2019, issued as U.S. Pat. No. 11,219,451 on Jan. 11, 2022.

As shown in FIG. 10, staple cartridge (200) includes a cartridge body (202) having an upwardly facing deck (204), an elongate slot (206) extending along a central axis of cartridge body (202) and opening upwardly through deck (204), and a plurality of staple openings (208) extending through deck (204) on each side of elongate slot (206). As shown in FIGS. 16A-16D described below, each staple opening (208) slidably houses an unformed staple (222) similar to staple (80) and having a pair of legs (224), and a respective staple driver (226) configured to drive the staple (222) outwardly toward anvil (56) to be formed. A lower tray (210) of staple cartridge (200) retains the staples (222) and staple drivers (226) within cartridge body (202).

Cartridge body (202) of the present example further includes a plurality of upwardly-opening recesses (212, 214, 216) formed in deck (204) and having base surfaces through which staple openings (208) extend. More specifically, on each side of elongate slot (206), deck (204) includes an inner row of triangular recesses (212) each having a medial apex that points transversely away from elongate slot (206); an outer row of triangular recesses (214) each having a medial apex that points transversely toward elongate slot (206); and a middle row of diamond-shaped recesses (216) each having an inner medial apex that points transversely toward elongate slot (206) and an opposed outer medial apex that points transversely away from elongate slot (206). Recesses (212, 214, 216) may cooperate to more securely grip and thereby stabilize clamped tissue during stapling and cutting of the clamped tissue.

Cartridge body (202) of the present example further includes a plurality of elongate tabs (218) projecting laterally outwardly from deck (204) on each lateral side of cartridge body (202). Tabs (218) of the present example are spaced apart from one another in a longitudinal direction, and each tab (218) has a generally rounded rectangular shape. Cartridge body (202) further includes a plurality of attachment openings (220) spaced apart from one longitudinally on each side of elongate slot (206), with each attachment opening (220) being smaller than a staple opening (208) and having a hexagonal shape. In the present version, each tab (218) includes at least one attachment opening (220). Attachment openings (220) may be configured to facilitate releasable attachment of an adjunct, such as adjunct (230), to staple cartridge deck (204).

Adjunct (230) has a plurality of sub-structures in the form of three-dimensional, resiliently compressible (or collapsible) nodules (232) that define a lower portion of adjunct (230) and are integrally connected with one another, via an upper portion (233) of adjunct (230), in a plurality of linear arrays defining a lattice structure having an elongate rectangular shape. In the present example, adjunct (230) includes four axial rows of nodules (232) each extending in a proximal-distal direction to define a length of adjunct (230), and sixteen transverse rows of nodules (232) each extending in a direction transverse to a length of staple cartridge (200) to define a transverse width of adjunct (230). It will be appreciated that adjunct (230) of other versions may have various other quantities and configurations of nodules (232).

Each nodule (232) of the present example has a generally cuboid shape defining four side surfaces (234), a lower surface (236), and an opening (238) in lower surface (236) that extends along a vertical central axis (A1) of nodule (232) and defines an open, hollow interior of nodule (232).

Additionally, each nodule (232) is symmetrical about its centroid along a second axis (A2) of nodule (232) that extends horizontally in a proximal-distal direction parallel to the length of adjunct (230), and along a third axis (A3) of nodule (232) that extends horizontally in a direction traverse to the length of adjunct (230), where each axis (A1, A2, A3) extends through the centroid. It will be appreciated that nodules (232) may be alternatively shaped in other versions of adjunct (230). Though not shown, in some versions one or more of side surfaces (234) of each nodule (232) may include an opening that communicates with the hollow interior of the nodule (232). Additionally, in some versions, adjacent nodules (232) may be interconnected at side surfaces (234) by connecting structures, which may define respective lumens between the hollow interiors of adjacent nodules (232).

Adjunct (230) may be formed of an elastic, bioabsorbable polymeric material having a suitable degree of elasticity that enables adjunct (230) to compress and resiliently resume its original shape. In the present example, each nodule (232) of adjunct (230) is resiliently compressible in such a manner along at least each of its three axes (A1, A2, A3). Additionally, adjunct (230) may be formed as a monolithic structure via an additive manufacturing process, for example. It will be appreciated that adjunct (230) may be further or alternatively constructed and operable in accordance with any of the other teachings made herein, and/or with the teachings of any of the patent references incorporated by reference here.

Adjunct (230) may be releasably attached to a deck of a staple cartridge, such as decks (74, 204) of staple cartridges (70, 200), via one or more attachment features, examples of which are described in greater detail below. It will be appreciated that adjunct (230) may be attached to a staple cartridge with or without an applicator device.

IV. Exemplary Alternative Compressible Adjunct

As described above in connection with FIGS. 10-12, adjunct (230) includes a plurality of three-dimensional resiliently compressible nodules (232), each of which is resiliently compressible along each of its three axes (A1, A2, A3) when clamped by end effector (50) against tissue (T). Accordingly, each nodule (232) is configured to apply a spring force along each of its three axes (A1, A2, A3) when compressed with tissue. In some instances, it may be desirable to provide a compressible adjunct that is resiliently compressible during closure of end effector (50) but without deforming in a direction transverse to the length of staple cartridge (200), such as along third axis (A3) of nodules (232), to promote optimal alignment of the legs of staples (80) with staple forming pockets (58) of anvil (56) during firing. As described below, FIGS. 13-16D show an exemplary alternative adjunct (240) that is configured is such a manner and for use with surgical stapler (10). In particular, during closure of end effector (50), each of the resiliently compressible members of adjunct (240) is independently compressible in height without deforming in width in a direction transverse to the length of staple cartridge (200).

While adjunct (240) is shown and described herein as being suitably shaped and configured for use with linear staple cartridge (200), it will be appreciated that in other versions adjunct (240) may be alternatively shaped and configured for use with various other types of staple cartridges and surgical staplers. By way of example only, such other staple cartridges and surgical staplers may be of the types disclosed in U.S. Pat. No. 10,709,452, entitled "Methods and Systems for Performing Circular Stapling," issued Jul. 14, 2020; U.S. patent application Ser. No. 16/945,042, entitled "Features to Enhance Staple Heigh Consistency in Curved Surgical Stapler," filed Jul. 31, 2020; and U.S. Pat. No. 11,033,266, entitled "Decoupling Mechanism for Linear Surgical Stapler," issued Jun. 15, 2021, the disclosures of which are incorporated by reference herein.

Figure 13:
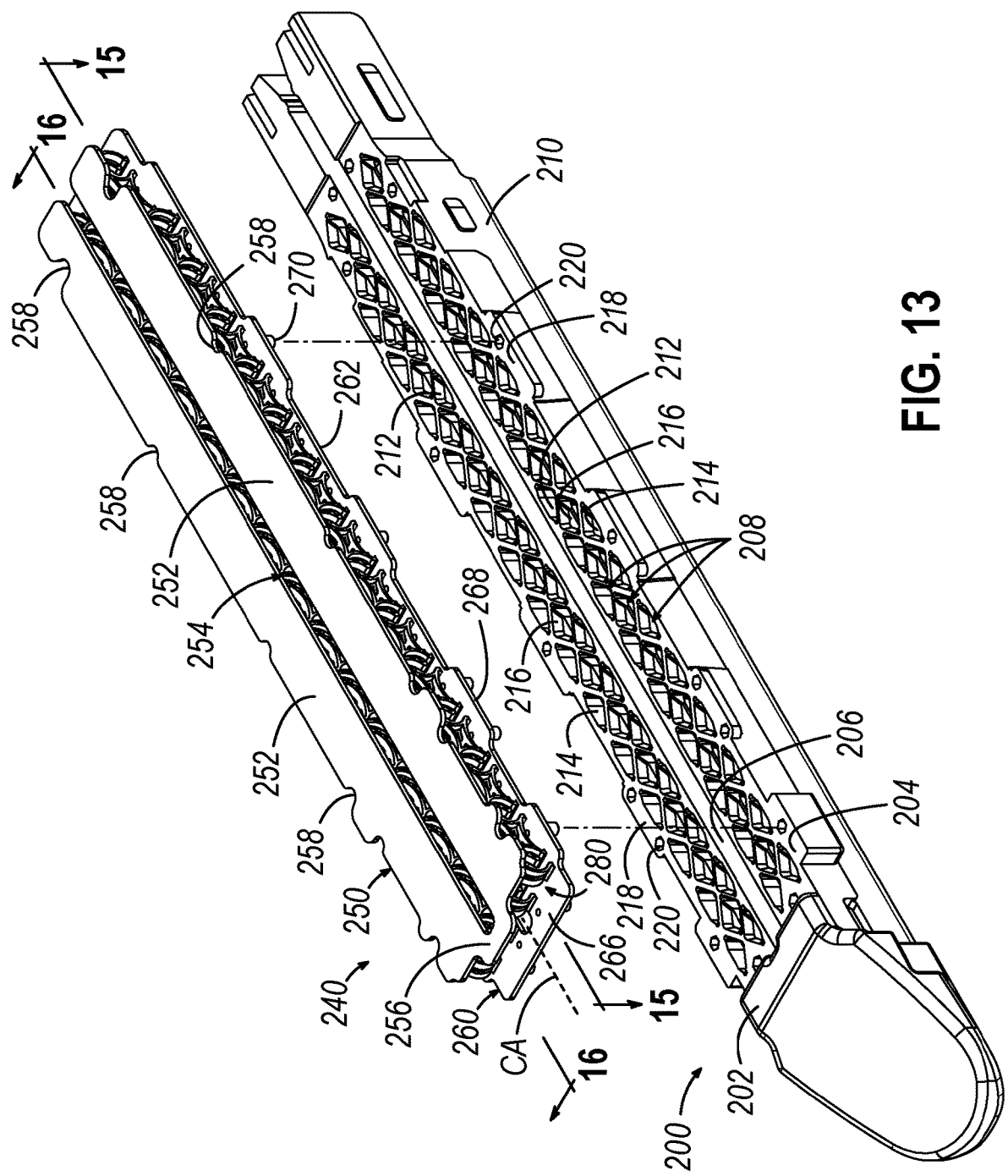
FIG. 13 depicts a disassembled perspective view of another exemplary adjunct in combination with the staple cartridge of FIG. 10.
Figure 14:
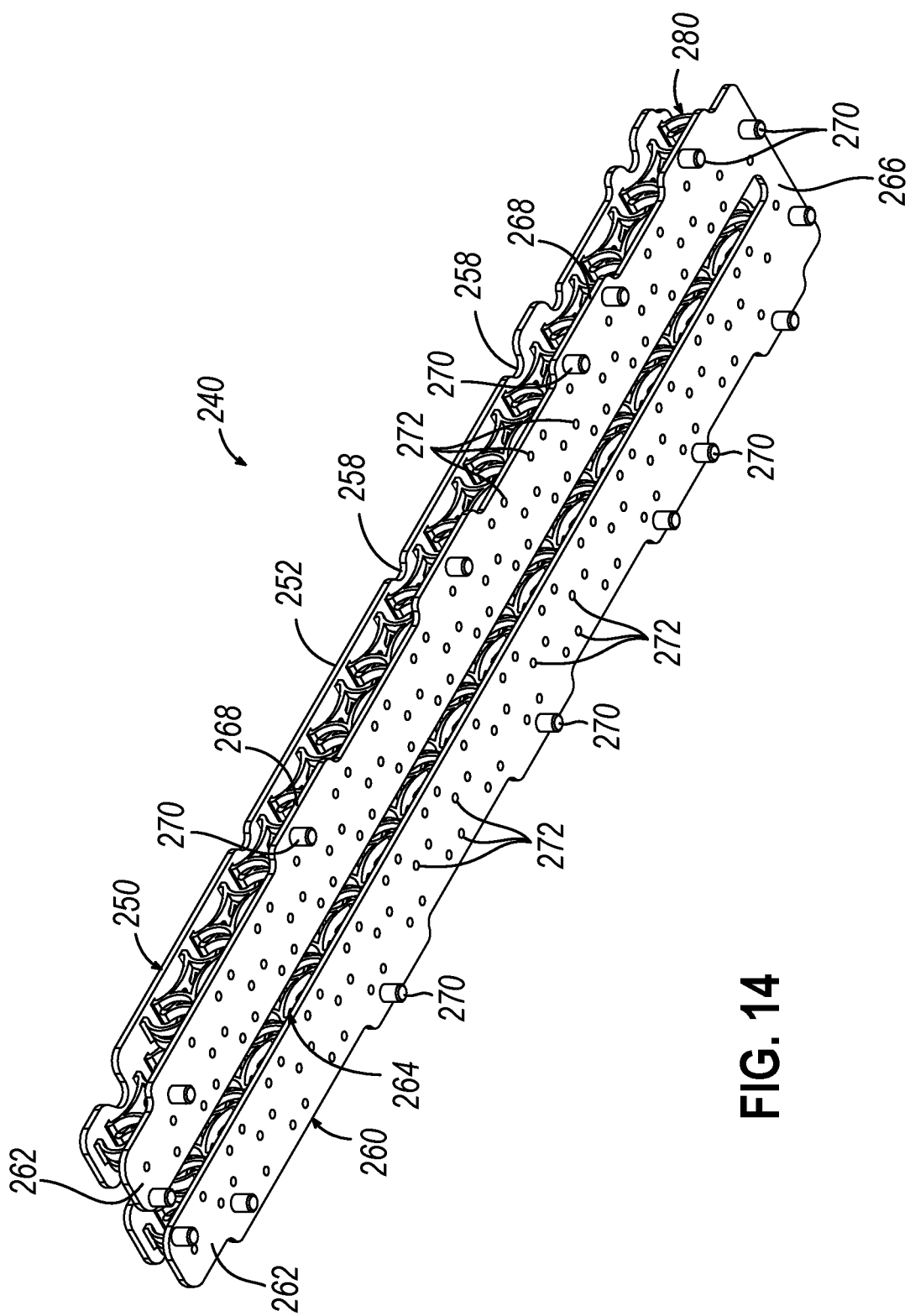
FIG. 14 depicts a lower perspective view of the adjunct of FIG. 13.
Figure 15:
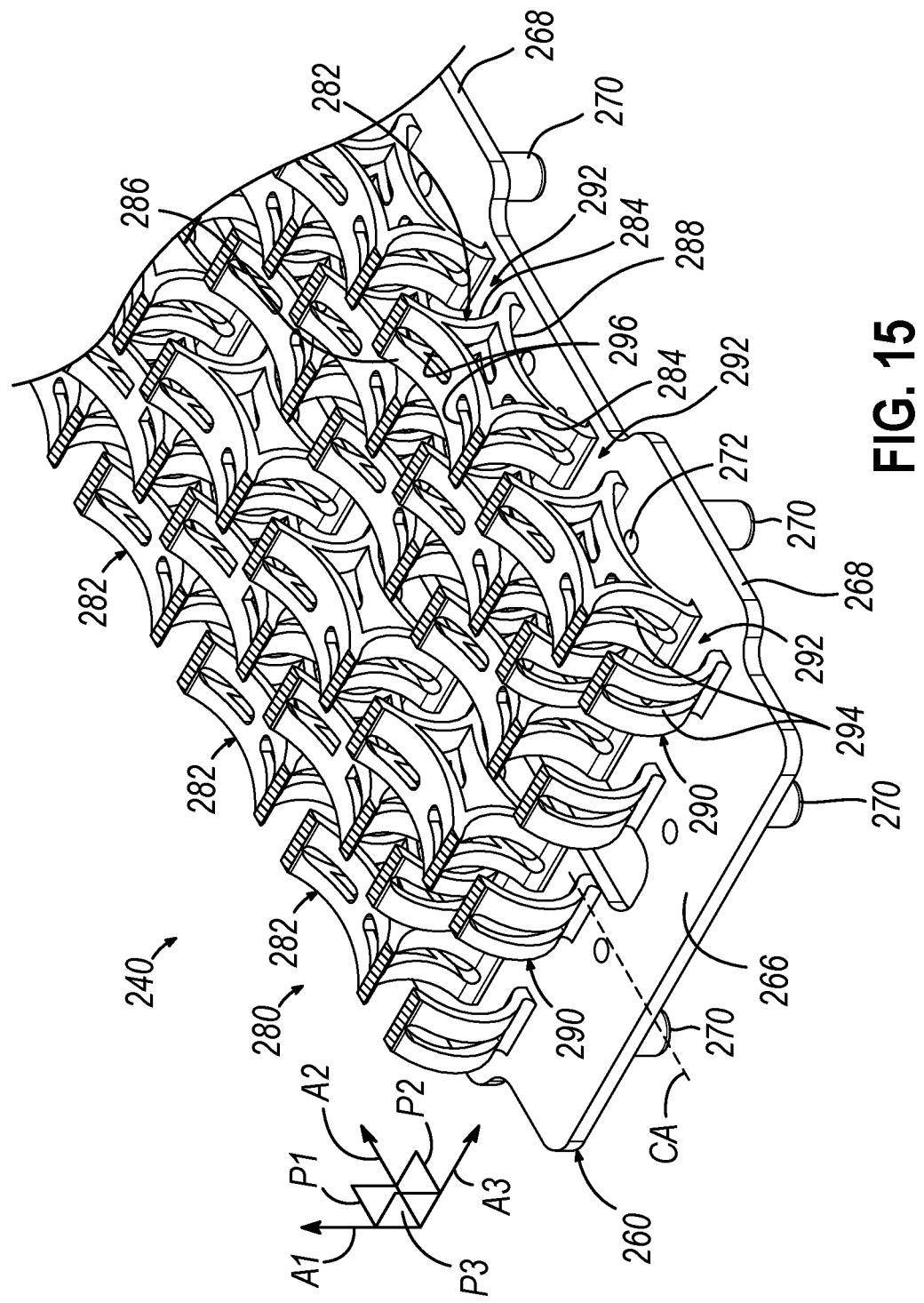
FIG. 15 depicts a cross-sectional perspective view of a proximal end portion of the adjunct of FIG. 13, taken along section line 15-15 of FIG. 13.

As shown in FIGS. 13-15, adjunct (240) of the present example includes an upper body in the form of a flexible upper panel (250), a lower adjunct body in the form of a flexible lower panel (260), and a resiliently compressible lattice (280) interposed between and integrally connected with upper and lower panels (250, 260) such that panels (250, 260) and lattice (280) collectively define a unitary, monolithic structure. Panels (250, 260) and lattice (280) may be formed of a common material, such as any suitable resilient biocompatible material. In other versions, one or both panels (250, 260) may be formed of a different material than lattice (280), and/or one both panels (250, 260) may be formed independently from lattice (280) and later coupled with lattice (280). Additionally, in other versions, adjunct (240) may include one or more additional layer, such as those described above in connection with buttress assemblies (110, 112) of FIGS. 7-9.

As shown best in FIG. 13, upper panel (250) of adjunct (240) includes a pair of upper elongate side portions (252) that are spaced apart by an upper longitudinal gap (254) and are interconnected at their distal ends by an upper distal bridge element (256) that defines a distal end of upper panel (250). Additionally, each upper elongate side portion (252) may include a plurality of notches (258) formed in its outer edge and spaced apart along its length. Each notch (258) aligns with a respective post (270) extending downwardly from lower panel (260), described below, and may provide clearance for post (270) when adjunct (240) is compressed by end effector (50), as described below.

Similarly, as shown best in FIG. 14, lower panel (260) of adjunct (240) includes a pair of lower elongate side portions (262) that are spaced apart by a lower longitudinal gap (264) and are interconnected at their distal ends by a lower distal bridge element (266) that defines a distal end of lower panel (260). Upper and lower longitudinal gaps (254, 264) extend along a longitudinal central axis (CA) of adjunct (240) and thus are configured to align with and overlie elongate slot (206) of staple cartridge (200) when adjunct (240) is coupled with staple cartridge (200). Each lower elongate side portion (262) includes a plurality of tabs (268) that extend laterally outwardly from the outer edge of lower elongate side portion (262) and are spaced apart along the length of adjunct (240). Each tab (268) is shape similarly to and is configured to align with and overlie a respective tab (268) of staple cartridge (200).

Lower panel (260) of adjunct (240) further includes a plurality of attachment features in the form of cylindrical posts (270) that extend downwardly from an underside of lower panel (260) and are spaced apart along the outer edges of lower elongate side portions (262). In the present version, at least one post (270) extends downwardly from the underside of each tab (268). Each post (270) is configured to align with and be received by a respective opening (220) of staple cartridge (200) with a press-fit engagement to thereby releasably couple adjunct (240) with cartridge deck (204). It will be appreciated that in other versions adjunct (240) may include attachment features of various other types suitable for releasably coupling adjunct (240) with a stapling surface of a surgical stapler end effector.

As shown best in FIGS. 15 and 16A-16D, lattice (280) of adjunct (240) includes a plurality of resiliently compressible members (282) that are arranged discretely in a plurality of linear arrays along a length of adjunct (240) between upper panel (250) and lower panel (260). As described in greater detail below, each resiliently compressible member (282) is configured to cooperate with a longitudinally adjacent resiliently compressible member (282) to apply a compression spring force to a respective staple (222) (see FIGS. 16A-16D) ejected by staple cartridge (200) vertically through adjunct (240). Accordingly, similar to adjunct (230) of FIGS. 10-12, adjunct (240) is configured to apply an individual spring force to each staple (222) along the length of the resulting formed staple pattern, thus ensuring a proper seal of tissue having a thickness that varies along a length of the formed staple pattern. However, unlike nodules (232) of adjunct (230), each resiliently compressible member (282) of adjunct (240) is configured to resiliently compress during closure of end effector (50) without deforming in a direction transverse to the arrays of resiliently compressible members (282) (i.e., transverse to longitudinal gaps (254, 264) of adjunct (240) and elongate slot (206) of staple cartridge (200)). Advantageously, this enables adjunct (240) to promote proper alignment of legs (224) of staples (222) with corresponding staple forming pockets (58) of anvil (56) during firing of surgical stapler (10), thus ensuring proper formation of staples (222) in tissue.

As shown in FIG. 15, each resiliently compressible member (282) of lattice (280) includes a pair of arcuate side elements (284) opposed from one another; an arcuate upper connecting element (286) that interconnects the upper portions of arcuate side elements (284); and an arcuate lower connecting element (288) opposed from upper connecting element (286) and that interconnects the lower portions of arcuate side elements (284). Arcuate elements (284, 286, 288) of a respective resiliently compressible member (282) are concavely curved toward one another, each in a direction toward a centroid (C) of the resiliently compressible member (282) (see FIGS. 16A-16D). Accordingly, arcuate elements (284, 286, 288) of each resiliently compressible member (282) collectively define a four-sided, lantern-shaped planar profile having an open interior in a vertical first plane (P1), which extends parallel to longitudinal gaps (254, 264) and is defined by a vertical first axis (A1) that intersects upper and lower panels (250, 260) and a horizontal second axis (A2) that extends parallel to panels (250, 260) and to longitudinal gaps (254, 264). This four-sided profile is extruded along a horizontal third axis (A3) that extends perpendicularly to the first and second axes (A1, A2), across a width of adjunct (240). Accordingly, each resiliently compressible member (282) has a height along the first axis (A1), a longitudinal length along the second axis (A2), and a transverse width along third axis (A3), with its length being greater than its width in the present example. As described below in connection with FIG. 16, each resiliently compressible member is configured to resiliently compress within the first plane (P1) without deforming along the third axis (A3) within the third plane (P3).

As shown best in FIGS. 13-15, adjunct (240) includes differently shaped resiliently compressible end members (290) at the proximal and distal ends of lattice (280). Each resiliently compressible end member (290) is similar in shape to an arcuate side element (284) of resiliently compressible members (282). In the present example, each resiliently compressible end member (290) is oriented such that its concave side faces toward a concave side of the longitudinally adjacent resiliently compressible member (282), and its convex side faces longitudinally outwardly in a proximal or distal direction.

As shown best in FIGS. 15 and 16A-16D, each resiliently compressible member (282) cooperates with a longitudinally adjacent resiliently compressible member (282), or a longitudinally adjacent resiliently compressible end member (290), to define a respective cylindrical spring structure (292). More specifically, each cylindrical spring structure (292) is defined by a confronting pair of arcuate side elements (284) of longitudinally adjacent resiliently compressible members (282), or by an arcuate side element (284) of a resiliently compressible member (282) in combination with a confronting resiliently compressible member (290) at a proximal or distal end of lattice (280). Each cylindrical spring structure (292) has a central axis (A) that extends along the transverse width of resiliently compressible members (282, 290), parallel to the third axis (A3) described above. Transversely adjacent linear arrays of resiliently compressible members (282, 290) are longitudinally offset from one another such that the central axis (A) of each cylindrical spring structure (292) in a first array aligns with the centroid (C) of a corresponding resiliently compressible member (282) in a transversely adjacent second array. However, as seen in FIG. 15, at the proximal-most and distal-most ends of lattice (280) there are no resiliently compressible members (282) positioned between transversely adjacent cylindrical spring structures (292) due to the longitudinal offset of the arrays described above. This longitudinal offset configuration is provided to accommodate the similar longitudinal offset configuration of staple openings (208) of staple cartridge (200). It will be appreciated that in other versions, resiliently compressible members (282, 290) may be arranged in various alternative configurations to accommodate alternative configurations of staple openings of a staple cartridge.

Each cylindrical spring structure (292) is configured to directly overlie and align with a respective staple opening (208) of staple cartridge (200). Accordingly, as described in greater detail below in connection with FIGS. 16C-16D, when staple cartridge (200) is fired by surgical stapler (10) the legs (224) of the respective staple (222) are configured to pass upwardly through adjunct (240) on either side of cylindrical spring structure (292), with staple legs (224) being formed about the cylindrical spring structure (292). This configuration enables cylindrical spring structure (292) to exert a compressive spring force on that staple (222) and the portion of tissue (T) captured by staple (222), thereby promoting an effective seal of tissue (T) by staple (222). Accordingly, adjunct (240) provides a cylindrical spring structure (292) for each staple (222) such that each staple (222) and its respective portion of tissue (T) receive a designated spring force applied by adjunct (240) to ensure effective sealing of stapled tissue (T) by formed staples (222).

As shown best in FIGS. 14-15, lower panel (260) of adjunct (240) includes a plurality of circular openings (272) each configured to align with a respective staple leg (224). Circular openings (272) permit staple legs (224) to slidably translate upwardly through lower panel (260) during firing of staple cartridge (200). In some versions, though not shown, upper panel (250) may include a similar arrangement of circular openings (272). As also shown in FIGS. 14-15, each resiliently compressible member (282, 290) includes one or more elongate slots each similarly configured to slidably receive a staple leg (224) upwardly therethrough during firing of staple cartridge (200). More specifically, each arcuate side element (284) and each resiliently compressible end member (290) includes an elongate vertical slot (294) that extends for nearly a full height of the side element (284) or end member (290). Additionally, each upper and lower connecting element (288) includes a pair of elongate horizontal slots (296), each of which is shorter than a vertical slot (294) of the same resiliently compressible member (282). Horizontal slots (296) are spaced longitudinally apart from one another to define a web between transversely adjacent portions of the respective upper or lower connecting element (288), thus maintaining a desired degree of structural rigidity for the upper or lower connecting element (288). Each elongate slot (294, 296) of a resiliently compressible member (282, 290) aligns with a respective circular opening (272) of lower panel (260) to facilitate passage of a respective staple leg (224). Accordingly, as shown in FIGS. 16B-16D described below, circular openings (272) and elongate slots (294, 296) cooperate to facilitate passage of staple legs (224) upwardly through adjunct (240) with minimal resistance, thus enabling each staple leg (224) to remain aligned with its respective staple forming pocket (58) of anvil (56) throughout the firing process to ensure proper and optimal formation of staples (222) in tissue (T). Thus, it will be understood that each cooperative pair of circular openings (272) and overlying portions of elongate slots (294, 294) are spaced apart from one another by a distance equal to the width of a crown of staple (222).

Figure 16A:
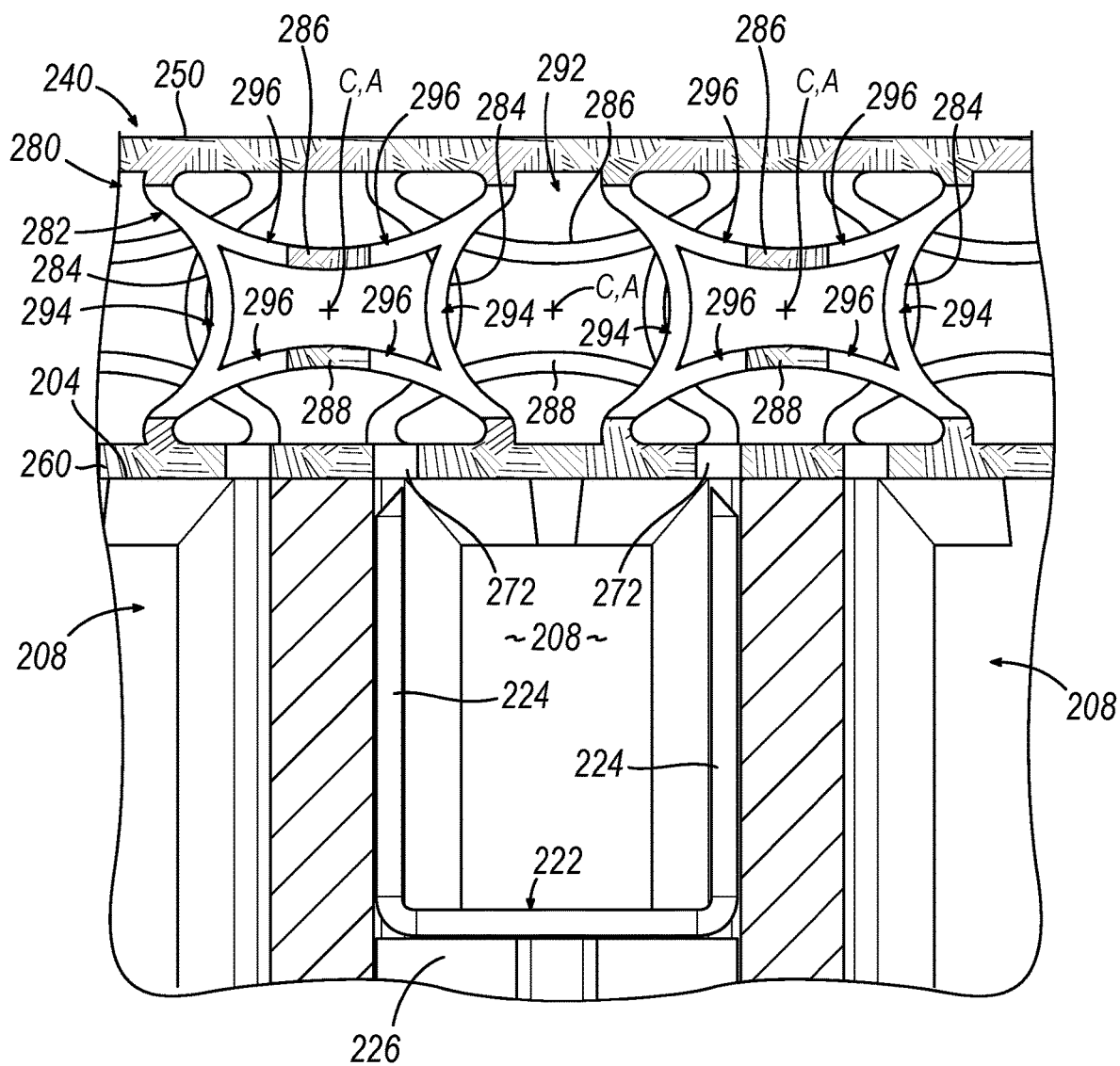
FIG. 16A depicts an assembled cross-sectional view of the adjunct and staple cartridge of FIG. 13, taken along section line 16-16 of FIG. 13, showing the adjunct in a non-compressed stated prior to closure of a corresponding surgical stapler end effector.
Figure 16B:
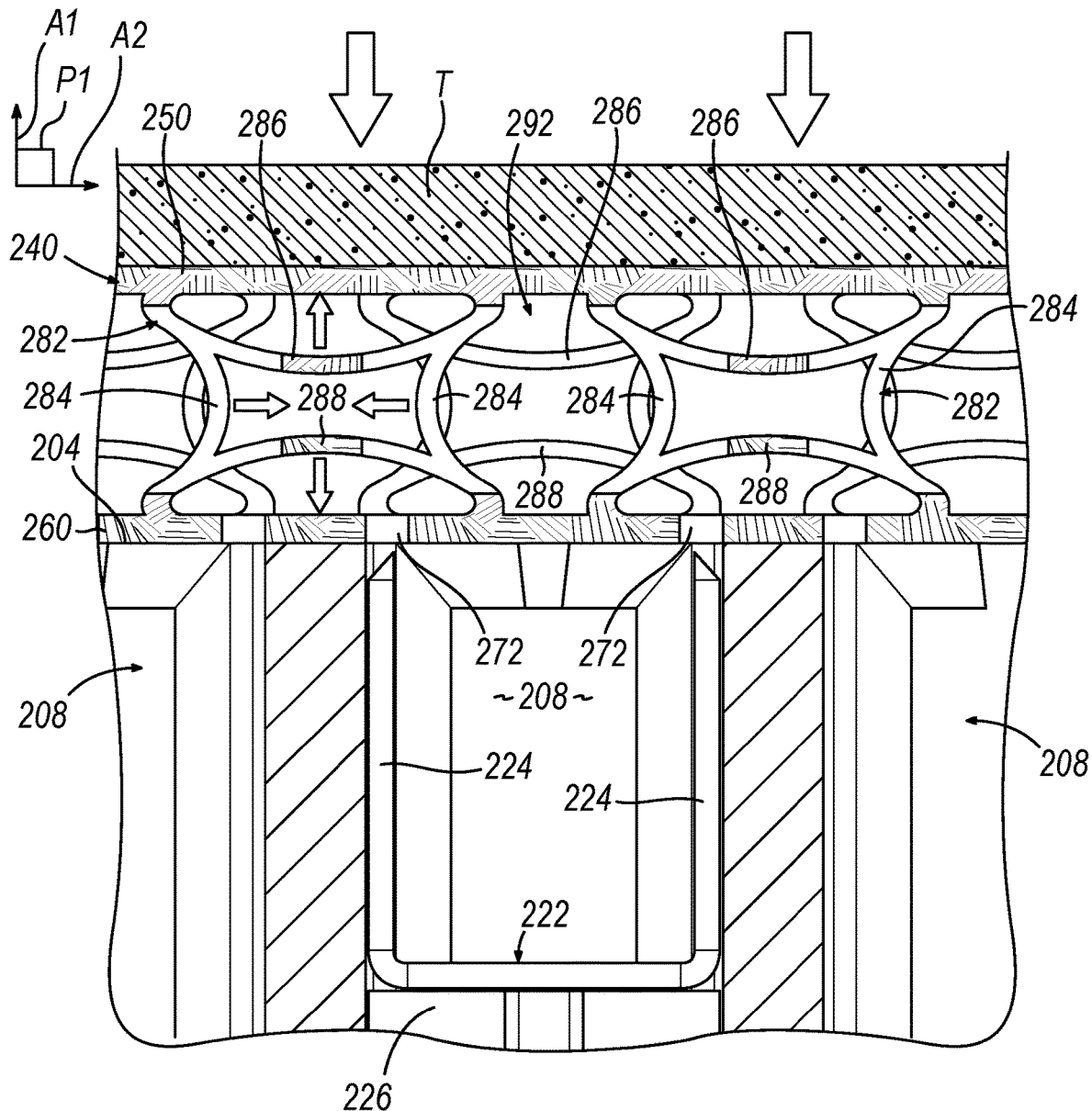
FIG. 16B depicts an assembled cross-sectional view of the adjunct and staple cartridge of FIG. 13, taken along section line 16-16 of FIG. 13, showing the adjunct and tissue in a compressed stated following closure of the corresponding surgical stapler end effector.
Figure 16C:
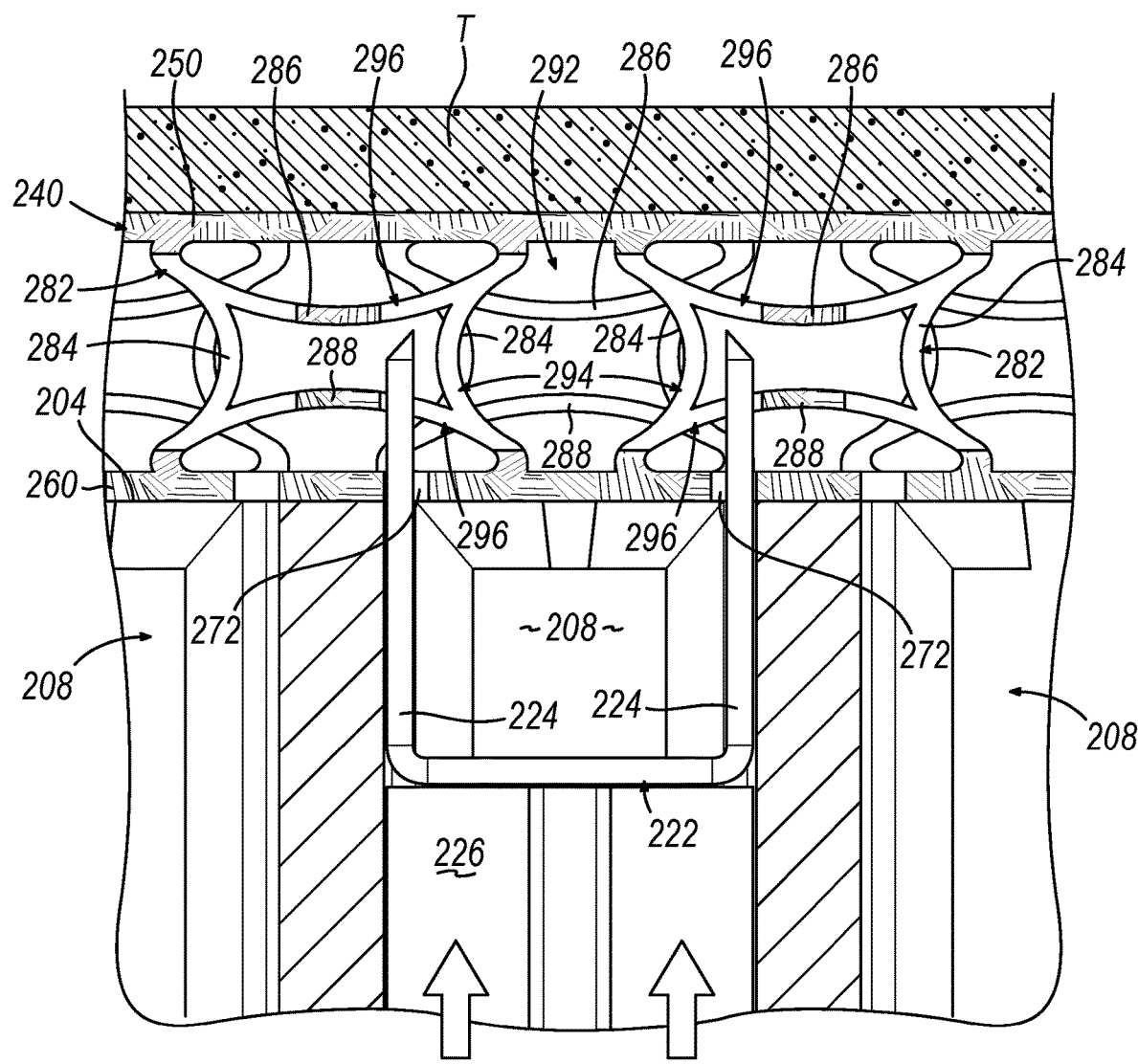
FIG. 16C depicts an assembled cross-sectional view of the adjunct and staple cartridge of FIG. 13, taken along section line 16-16 of FIG. 13, showing the adjunct in the compressed state and showing vertical advancement of a staple such that its legs pass through the adjunct during a firing stroke of the corresponding surgical stapler.
Figure 16D:
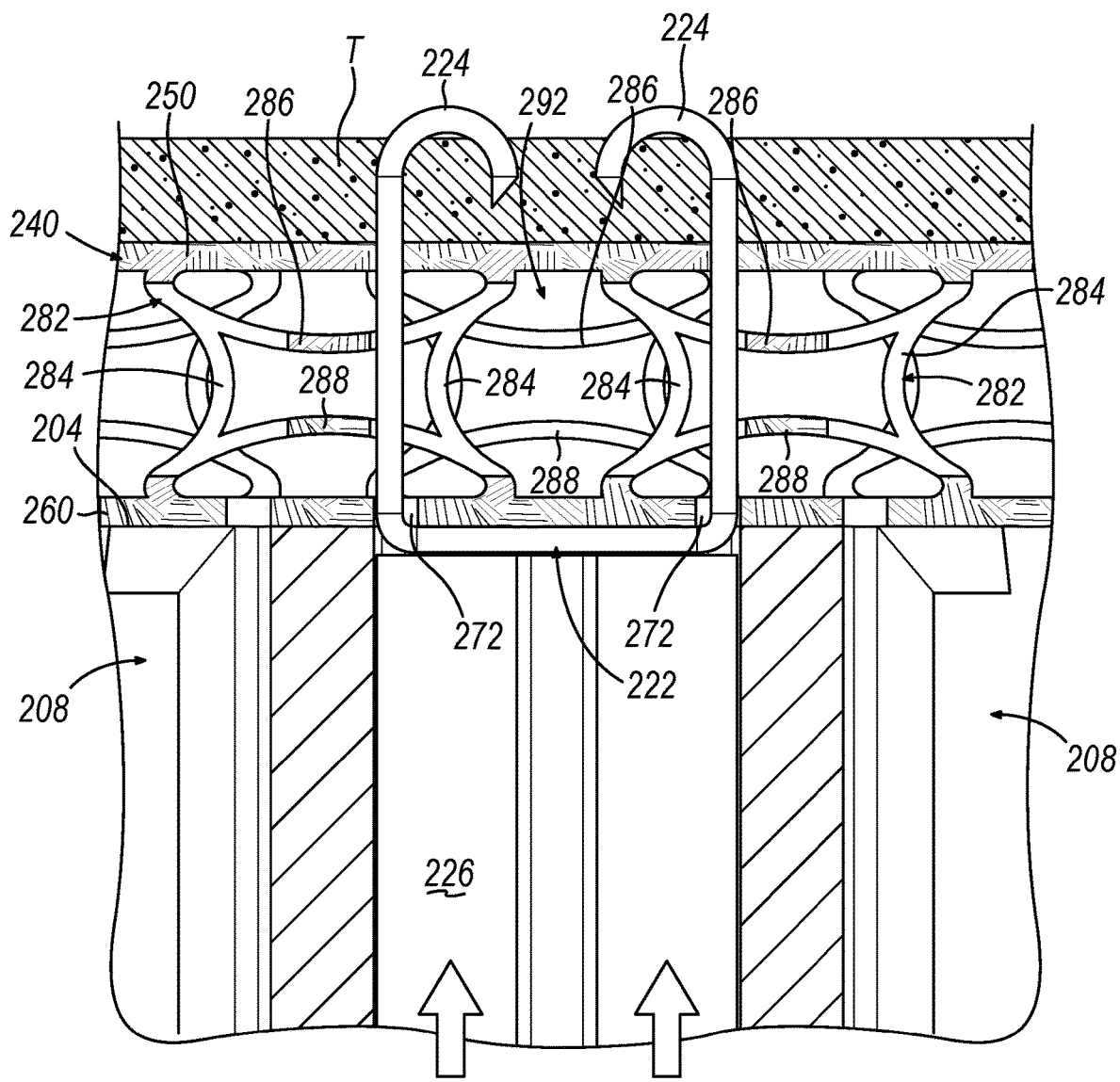
FIG. 16D depicts an assembled cross-sectional view of the adjunct and staple cartridge of FIG. 13, taken along section line 16-16 of FIG. 13, showing the adjunct in the compressed state and the staple legs having passed fully through the adjunct and formed in the tissue.

FIGS. 16A-16D show an exemplary use of adjunct (240) in connection with staple cartridge (200) and tissue (T). As shown in FIG. 16A, adjunct (240) is coupled to deck (204) of staple cartridge (200) in the manner described above such that lower panel (260) overlies and directly contacts deck (204). Additionally, each cylindrical spring structure (292) and corresponding pair of circular openings (272) in lower panel (260) of adjunct (240) is aligned with a respective staple opening (208) in deck (204). End effector (50) of surgical stapler (10) (see FIGS. 1-8) remains in an open state, prior to clamping of tissue (T).

As shown in FIG. 16B, end effector (50) has been positioned at a surgical site and a layer of tissue (T) has been clamped between lower and upper jaws (52, 54) of end effector (50) (see FIGS. 1-8) such that tissue (T) overlies upper panel (250) of adjunct (240) and a downward compressive force is exerted on tissue (T) and adjunct (240). As shown, resiliently compressible members (282) resiliently deform only in first plane (P1), such that the four-sided profile of each resiliently compressible member (282) generally flattens and elongates, without any lateral deformation of resiliently compressible members (282, 290) along third axis (A3) in third plane (P3) (see FIG. 15). Simultaneously, the circular shape of each cylindrical spring structure (292) generally flattens and elongates in the first plane (P1) as well. Advantageously, the intentional lack of transverse deformation by resiliently compressible members (282, 290) in the third plane (P3) ensures that elongate slots (294, 296) of resiliently compressible members (282, 290) remain aligned laterally with staple legs (224), which minimizes lateral resistance encountered by staple legs (224) as they pass upwardly through adjunct (240).

As shown in FIG. 16C, staple cartridge (200) is fired such that each staple driver (226) (only one being shown) drives a respective staple (222) (only one being shown) upwardly from the respective staple opening (208). Each leg (224) of each staple (222) passes upwardly through a respective circular opening (272) in lower panel (260) of adjunct (240), and subsequently upwardly through an interior space of lattice (280) defined by a pair of upper and lower horizontal slots (296) and a corresponding vertical slot (294) of a respective compressed resiliently compressible member (282) or alternatively a vertical slot (294) of a respective compressed end member (290), along the respective first plane (P1) (see FIGS. 15 and 16B). Accordingly, there is minimal to no contact between each staple leg (224) and lower panel (260) and resiliently compressible members (282, 290) in a compressed stated. Additionally, as described above, the legs (224) of each staple (222) advance upwardly along either side of a respective cylindrical spring structure (292), without contacting the cylindrical spring structure (292).

FIG. 16D shows staple cartridge (200) in a fully fired state in which each staple (222) has been driven fully upwardly through adjunct (240) and tissue (T) such that the ends of staple legs (224) have pierced through upper panel (250) of adjunct (240) and been formed by anvil (56) (see FIG. 3). Formed staples (222) maintain adjunct (240) in an at least partially compressed state even when end effector (50) is opened, such that each cylindrical spring structure (292) exerts a spring force against the respective staple (222) and portion of tissue (T), thus ensuring an effective seal of tissue (T) along the line of formed staples (222). As described above, the lack of deformation by resiliently compressible members (282, 290) laterally along third axis (A3) within third plane (P3) when adjunct (240) is clamped by end effector (50), in combination with the provision of circular openings (272) in lower panel (260) and elongate slots (294, 296) in resiliently compressible members (282, 290), ensures minimal interference between adjunct (240) and staple legs (224) as staple legs (224) advance upwardly through adjunct (240) and toward their respective staple forming pockets (58) of anvil (56) during firing. This ensures that proper alignment between staple legs (224) and pockets (58) is maintained during firing, thus ensuring proper formation of staple legs (224).

V. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An adjunct configured for use with a surgical stapler end effector, comprising: (a) an adjunct body configured to overlie and directly contact a stapling surface of a surgical stapler end effector; and (b) a plurality of resiliently compressible members coupled with the adjunct body, wherein each resiliently compressible member extends away from the adjunct body in a first plane that intersects the adjunct body and along which the resiliently compressible member is configured to receive a respective staple of the surgical stapler end effector, wherein in response to closure of the surgical stapler end effector, each resiliently compressible member is configured to resiliently compress within the first plane without deforming in a second plane that perpendicularly intersects the first plane.

Example 2

The adjunct of Example 1, wherein the resiliently compressible members are spaced apart from one another.

Example 3

The adjunct of any of the preceding Examples, wherein each of the resiliently compressible members includes a pair of side legs and upper and lower connecting elements that interconnect the side legs and are spaced apart from the adjunct body, wherein the side legs and the upper and lower connecting elements of each resiliently compressible member cooperate to define a four-sided shape.

Example 4

The adjunct of Example 3, wherein each of the side legs and each of the upper and lower connecting elements is arcuate.

Example 5

The adjunct of any of Examples 3 through 4, wherein each of the side legs and each of the upper and lower connecting elements is concavely curved in a direction toward a centroid of the resiliently compressible member.

Example 6

The adjunct of any of the preceding Examples, wherein each of the resiliently compressible members includes an arcuate end feature that confronts the arcuate end feature of an adjacent resiliently compressible member to define a respective cylindrical resilient structure having a central axis that extends parallel to the adjunct body.

Example 7

The adjunct of Example 6, wherein each of the cylindrical resilient structures has a circular shape that is configured to elongate in a direction transverse to the central axis of the cylindrical resilient structure when the resiliently compressible members compress in response to closure of the surgical stapler end effector.

Example 8

The adjunct of any of Examples 6 through 7, wherein the resiliently compressible members are arranged in a first array and a second array spaced apart from one another, wherein the resiliently compressible members of the first array are offset from the resiliently compressible members of the second array such that each resiliently compressible member of the first array aligns with a respective cylindrical resilient structure of the second array along a shared central axis and such that each resiliently compressible member of the second array aligns with a respective cylindrical resilient structure of the first array along a shared central axis, wherein the shared central axes extend transversely to the first and second arrays.

Example 9

The adjunct of any of the preceding Examples, wherein each of the resiliently compressible members has a length in a first direction parallel to the adjunct body and a width in a second direction parallel to the adjunct body, wherein the length is greater than the width.

Example 10

The adjunct of any of the preceding Examples, wherein each of the resiliently compressible members includes an elongate slot configured to receive a staple leg therethrough when the surgical stapler end effector is fired.

Example 11

The adjunct of Example 10, wherein the adjunct body includes a plurality of openings that align with the elongate slots of the resiliently compressible members, wherein each opening is configured to receive a respective staple leg therethrough when the surgical stapler end effector is fired.

Example 12

The adjunct of any of the preceding Examples, wherein the adjunct body comprises a lower panel, wherein the adjunct further comprises an upper panel spaced apart from the lower panel, wherein the resiliently compressible members are interposed between and integrally connected with the upper and lower panels.

Example 13

The adjunct of any of the preceding Examples, wherein the adjunct body includes a plurality of protrusions configured to be received within corresponding openings formed in the stapling surface of the surgical stapler end effector to thereby couple the adjunct with the surgical stapler end effector.

Example 14

An apparatus comprising: (a) a stapling surface having a plurality of openings configured to house staples or a plurality of staple forming pockets configured to form staples; and (b) the adjunct of claim 1, wherein the adjunct is configured to overlie and directly contact the stapling surface.

Example 15

An apparatus comprising: (a) a first stapling surface having a plurality of staple openings that house a plurality of staples; (b) a second stapling surface having a plurality of staple forming pockets configured to form the staples, wherein the first and second stapling surfaces are configured to cooperate to clamp and staple tissue; and (c) the adjunct of claim 1, wherein the adjunct is configured to overlie and directly contact one of the first stapling surface or the second stapling surface, wherein the adjunct is configured to receive the staples therethrough.

Example 16

An adjunct configured for use with a surgical stapler end effector, comprising: (a) an upper body; (b) a lower body spaced apart from the upper body, wherein the lower body is configured to overlie and directly contact a stapling surface of a surgical stapler end effector; and (c) a lattice interposed between the upper and lower bodies and comprising a plurality of resiliently compressible members, wherein in response to closure of the surgical stapler end effector, each of the resiliently compressible members is configured to resiliently compress along a first axis that intersects each of the upper and lower bodies without deforming along a second axis that perpendicularly intersects the first axis and that extends parallel to at least one of the upper or lower bodies.

Example 17

The adjunct of Example 16, wherein the upper body comprises an upper panel and the lower body comprises a lower panel, wherein the lattice is integrally connected with each of the upper and lower panels.

Example 18

An adjunct configured for use with a surgical stapler end effector, comprising: (a) a first array of resiliently compressible members, wherein each resiliently compressible member of the first array includes an arcuate end feature that confronts the arcuate end feature of an adjacent resiliently compressible member of the first array to define a respective cylindrical resilient structure; and (b) a second array of resiliently compressible members that extends alongside the first array of resiliently compressible members, wherein each resiliently compressible member of the second array includes an arcuate end feature that confronts the arcuate end feature of an adjacent resiliently compressible member of the second array to define a respective cylindrical resilient structure, wherein the resiliently compressible members of the first array are offset from the resiliently compressible members of the second array such that each resiliently compressible member of the first array aligns with a respective cylindrical resilient structure of the second array along a respective axis that extends transversely to each of the first and second arrays.

Example 19

The adjunct of Example 18, wherein each resiliently compressible member of the second array aligns with a respective cylindrical resilient structure of the first array along a respective axis that extends transversely to each of the first and second arrays.

Example 20

The adjunct of any of Examples 18 through 19, wherein each resiliently compressible member is configured to receive a staple leg therethrough in a first direction defining a height of the resiliently compressible member, wherein in response to closure of the surgical stapler end effector each resiliently compressible member is configured to resiliently compress in the first direction without deforming in a second direction that is perpendicular to the first direction and parallel to the respective axis.

VI. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Furthermore, any one or more of the teachings herein may be combined with any one or more of the teachings disclosed in U.S. patent application Ser. No. 17/514,073, entitled "Displaceable Adjunct Attachment Features for Surgical Stapler," filed on Oct. 29, 2021, published as U.S. Pat. Pub. No. 2023/0139479 on May 4, 2023; and U.S. patent application Ser. No. 17/514,096, entitled "Discrete Adjunct Attachment Features for Surgical Stapler," filed on Oct. 29, 2021, published as U.S. Pat. Pub. No. 2023/0139613 on May 4, 2023, the disclosures of which are incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, California.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. An adjunct configured for use with a surgical stapler end effector, comprising:
   (a) an adjunct body configured to overlie and directly contact a stapling surface of a surgical stapler end effector, wherein the adjunct body defines a longitudinal axis; and
   (b) a plurality of resiliently compressible members coupled with the adjunct body, wherein each resiliently compressible member extends away from the adjunct body in a first plane that intersects the adjunct body and along which the resiliently compressible member is configured to receive a respective staple of the surgical stapler end effector,
   wherein each of the resiliently compressible members is positioned in a row parallel to the longitudinal axis and is longitudinally spaced apart from the other resiliently compressible members positioned within the same row, wherein in response to closure of the surgical stapler end effector, each resiliently compressible member is configured to resiliently compress within the first plane without deforming in a second plane that perpendicularly intersects the first plane, wherein each of the resiliently compressible members includes a pair of side legs and upper and lower connecting elements that interconnect the side legs and are spaced apart from the adjunct body, wherein the side legs and the upper and lower connecting elements of each resiliently compressible member cooperate to define a four-sided shape having a single open interior.

2. The adjunct of claim 1, wherein each of the side legs and each of the upper and lower connecting elements is arcuate.

3. The adjunct of claim 1, wherein each of the side legs and each of the upper and lower connecting elements is concavely curved in a direction toward a centroid of the resiliently compressible member.

4. The adjunct of claim 1, wherein each of the resiliently compressible members includes an arcuate end feature that confronts the arcuate end feature of an adjacent resiliently compressible member to define a respective cylindrical resilient structure having a central axis that extends perpendicular to the longitudinal axis of the adjunct body.

5. The adjunct of claim 4, wherein each of the cylindrical resilient structures has an arcuate shape that is configured to elongate in a direction transverse to the central axis of the cylindrical resilient structure when the resiliently compressible members compress in response to closure of the surgical stapler end effector.

6. The adjunct of claim 4, wherein the resiliently compressible members are arranged in a first array and a second array spaced apart from one another, wherein the resiliently compressible members of the first array are offset from the resiliently compressible members of the second array such that each resiliently compressible member of the first array aligns with a respective cylindrical resilient structure of the second array along a shared central axis and such that each resiliently compressible member of the second array aligns with a respective cylindrical resilient structure of the first array along a shared central axis, wherein the shared central axes extend transversely to the first and second arrays.

7. The adjunct of claim 1, wherein each of the resiliently compressible members has a length in a first direction parallel to the adjunct body and a width in a second direction perpendicular to the longitudinal axis of the adjunct body, wherein the length is greater than the width.

8. The adjunct of claim 1, wherein each of the resiliently compressible members includes an elongate slot configured to receive a staple leg therethrough when the surgical stapler end effector is fired.

9. The adjunct of claim 8, wherein the adjunct body includes a plurality of openings that align with the elongate slots of the resiliently compressible members, wherein each opening is configured to receive a respective staple leg therethrough when the surgical stapler end effector is fired.

10. The adjunct of claim 1, wherein the adjunct body comprises a lower panel, wherein the adjunct further comprises an upper panel spaced apart from the lower panel, wherein the resiliently compressible members are interposed between and integrally connected with the upper and lower panels.

11. The adjunct of claim 1, wherein the adjunct body includes a plurality of protrusions configured to be received within corresponding openings formed in the stapling surface of the surgical stapler end effector to thereby couple the adjunct with the surgical stapler end effector.

12. An apparatus comprising:
(a) a stapling surface having a plurality of openings configured to house staples or a plurality of staple forming pockets configured to form staples; and
(b) the adjunct of claim 1, wherein the adjunct is configured to overlie and directly contact the stapling surface.

13. An apparatus comprising:
(a) a first stapling surface having a plurality of staple openings that house a plurality of staples;
(b) a second stapling surface having a plurality of staple forming pockets configured to form the staples, wherein the first and second stapling surfaces are configured to cooperate to clamp and staple tissue; and
(c) the adjunct of claim 1, wherein the adjunct is configured to overlie and directly contact one of the first stapling surface or the second stapling surface, wherein the adjunct is configured to receive the staples therethrough.

14. An adjunct configured for use with a surgical stapler end effector, comprising:
(a) an adjunct body including first and second planar body portions, wherein the first planar body portion is configured to overlie and directly contact a stapling surface of a surgical stapler end effector, wherein the second planar body portion is configured to directly contact tissue, wherein the adjunct body defines a longitudinal axis; and
(b) a plurality of discrete compressible structures, wherein each of the discrete compressible structures is directly coupled with the first and second planar bodies, wherein the discrete compressible structures are positioned within a first plane, wherein the first plane extends parallel to the longitudinal axis and intersects the first and second planar bodies, wherein each discrete compressible structure is configured to receive a leg of a staple,
wherein a discrete compressible structure of the plurality of discrete compressible structures includes a first opening configured to receive a leg of a first staple and a second opening configured to receive a leg of a second staple,
wherein in response to closure of the surgical stapler end effector, each discrete compressible structure is configured to resiliently compress within the first plane without deforming in a second plane that extends perpendicularly to the first plane and the longitudinal axis.

15. The adjunct of claim 14 in combination with a surgical stapler end effector having a first staple and a second staple each having a pair of legs.

16. The adjunct of claim 14, wherein one of the first or second planar body portions includes a plurality of apertures positioned within the first plane and each aperture is configured to receive a leg of a staple, wherein the other of the first or second planar body portions includes a continuous planar surface.

17. The adjunct of claim 16, wherein one of the first or second planar body portions also includes a plurality of protrusions configured to be received within corresponding openings formed in the stapling surface of the surgical stapler end effector to thereby couple the adjunct with the surgical stapler end effector.

18. An adjunct configured for use with a surgical stapler end effector, comprising:

(a) an adjunct body including upper and lower panels, wherein the adjunct body defines a longitudinal central axis, wherein the lower panel is configured to overlie and directly contact a stapling surface of a surgical stapler end effector;
(b) a first row of resiliently compressible structures positioned on a first side of the longitudinal central axis, wherein each of the resiliently compressible structures is directly coupled to each of the upper and lower panels without being directly coupled to any of the immediately adjacent resiliently compressible members, wherein each of the resiliently compressible structures includes a length extending parallel to the longitudinal central axis and a width extending non-parallel to the longitudinal central axis, wherein the length is greater than the width; and
(c) a second row of resiliently compressible structures positioned on the first side of the longitudinal central axis and spaced apart from the first row of resiliently compressible structures, wherein the second row is directly coupled to the upper and lower panels and is positioned parallel and adjacent to the first row of resiliently compressible structures,
wherein the first row of resiliently compressible structures includes a first resiliently compressible structure and the second row of resiliently compressible structures includes a second resiliently compressible structure, wherein the second resiliently compressible structure is staggered longitudinally relative to the first resiliently compressible structure so that the first resiliently compressible structure does not align with the second resiliently compressible structure in a direction transverse to the longitudinal central axis,
wherein in response to closure of the surgical stapler end effector, each resiliently compressible structure is configured to expand in a longitudinal direction parallel to the longitudinal central axis without deforming in a lateral direction perpendicular to the longitudinal central axis.

19. The adjunct of claim 18, further comprising a third row of resiliently compressible structures positioned on the first side of the longitudinal central axis, wherein the third row is directly coupled to the upper and lower panels, wherein the third row is positioned parallel and adjacent to the second row of resiliently compressible structures.

20. The adjunct of claim 19, wherein each of the resiliently compressible structures includes a proximal concave side, a distal concave side, and a pair of connecting elements that interconnect the proximal and distal concave sides.

\* \* \* \* \*